(12) United States Patent
Foley et al.

(10) Patent No.: US 8,706,185 B2
(45) Date of Patent: *Apr. 22, 2014

(54) METHOD AND APPARATUS FOR SURGICAL NAVIGATION OF A MULTIPLE PIECE CONSTRUCT FOR IMPLANTATION

(75) Inventors: Kevin T. Foley, Memphis, TN (US); Stacy Sprouse, Brighton, CO (US); David A. Mire, Cordova, TN (US); John B. Clayton, Superior, CO (US); Mark W. Hunter, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/946,288

(22) Filed: Nov. 15, 2010

(65) Prior Publication Data

US 2011/0060216 A1   Mar. 10, 2011

Related U.S. Application Data

(63) Continuation of application No. 10/687,539, filed on Oct. 16, 2003, now Pat. No. 7,835,778.

(51) Int. Cl.
 *A61B 5/05*   (2006.01)
(52) U.S. Cl.
 USPC ............ 600/407; 606/61; 606/130; 606/86 A; 606/99; 606/104; 606/246; 600/424
(58) Field of Classification Search
 USPC ............ 600/424; 606/61, 130, 53, 54, 59, 60, 606/250–258, 260, 261, 277, 278, 279
 See application file for complete search history.

(56) References Cited

U.S. PATENT DOCUMENTS

| | | | |
|---|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |

(Continued)

FOREIGN PATENT DOCUMENTS

| | | |
|---|---|---|
| CA | 964149 | 3/1975 |
| DE | 3042343 A1 | 6/1982 |

(Continued)

OTHER PUBLICATIONS

"Prestige Cervical Disc System Surgical Technique", 12 pgs.

(Continued)

*Primary Examiner* — James Kish
(74) *Attorney, Agent, or Firm* — Harness, Dickey

(57) ABSTRACT

A method and apparatus for percutaneous and/or minimally invasive implantation of a construct. The construct may be implanted using a navigation system for planning and execution of a procedure. A plurality of portions of the construct may be interconnected using locations and paths determined and navigated with the navigation system.

22 Claims, 19 Drawing Sheets

(56) References Cited

U.S. PATENT DOCUMENTS

| | | |
|---|---|---|
| 3,439,256 A | 4/1969 | Kahne |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |

(56) References Cited

U.S. PATENT DOCUMENTS

| | | |
|---|---|---|
| 5,099,846 A | 3/1992 | Hardy |
| 5,102,412 A | 4/1992 | Rogozinski |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,437,669 A | 8/1995 | Yuan et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,484,437 A | 1/1996 | Michelson |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |

(56) References Cited

U.S. PATENT DOCUMENTS

| | | |
|---|---|---|
| 5,568,384 A | 10/1996 | Robb et al. |
| 5,568,809 A | 10/1996 | Ben-haim |
| 5,571,109 A | 11/1996 | Bertagnoli |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,740,808 A | 4/1998 | Panescu et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,772,661 A | 6/1998 | Michelson |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,964,796 A | 10/1999 | Imran |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |

(56) References Cited

U.S. PATENT DOCUMENTS

| | | |
|---|---|---|
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,194,639 B1 | 2/2001 | Botella et al. |
| 6,201,387 B1 | 3/2001 | Govari |
| 6,203,497 B1 | 3/2001 | Dekel et al. |
| 6,211,666 B1 | 4/2001 | Acker |
| 6,223,067 B1 | 4/2001 | Vilsmeier et al. |
| 6,226,548 B1 * | 5/2001 | Foley et al. .................. 600/426 |
| 6,233,476 B1 | 5/2001 | Strommer et al. |
| 6,246,231 B1 | 6/2001 | Ashe |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,314,310 B1 | 11/2001 | Ben-Haim et al. |
| 6,332,089 B1 * | 12/2001 | Acker et al. .................. 600/424 |
| 6,341,231 B1 | 1/2002 | Ferre et al. |
| 6,348,058 B1 * | 2/2002 | Melkent et al. ............... 606/130 |
| 6,351,659 B1 | 2/2002 | Vilsmeier |
| 6,381,485 B1 | 4/2002 | Hunter et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,430,434 B1 | 8/2002 | Mittelstadt |
| 6,434,415 B1 | 8/2002 | Foley et al. |
| 6,437,567 B1 | 8/2002 | Schenck et al. |
| 6,445,943 B1 | 9/2002 | Ferre et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,516,212 B1 | 2/2003 | Bladen et al. |
| 6,522,907 B1 | 2/2003 | Bladen et al. |
| 6,527,443 B1 | 3/2003 | Vilsmeier et al. |
| 6,530,929 B1 | 3/2003 | Justis et al. |
| 6,551,325 B2 | 4/2003 | Neubauer et al. |
| 6,584,174 B2 | 6/2003 | Schubert et al. |
| 6,609,022 B2 | 8/2003 | Vilsmeier et al. |
| 6,611,700 B1 | 8/2003 | Vilsmeier et al. |
| 6,640,128 B2 | 10/2003 | Vilsmeier et al. |
| 6,648,888 B1 | 11/2003 | Shluzas |
| 6,694,162 B2 | 2/2004 | Hartlep |
| 6,701,179 B1 | 3/2004 | Martinelli et al. |
| 7,083,621 B2 * | 8/2006 | Shaolian et al. ............. 606/86 A |
| 7,570,791 B2 | 8/2009 | Frank et al. |
| 7,835,778 B2 | 11/2010 | Foley et al. |
| 8,211,153 B2 * | 7/2012 | Shaolian et al. ............... 606/279 |
| 2001/0007918 A1 | 7/2001 | Vilsmeier et al. |
| 2001/0034480 A1 | 10/2001 | Rasche et al. |
| 2002/0095081 A1 | 7/2002 | Vilsmeier et al. |
| 2003/0011624 A1 * | 1/2003 | Ellis .............................. 345/646 |
| 2003/0187351 A1 | 10/2003 | Franck et al. |
| 2004/0024309 A1 | 2/2004 | Ferre et al. |

FOREIGN PATENT DOCUMENTS

| | | |
|---|---|---|
| DE | 3508730 | 9/1986 |
| DE | 3717871 | 12/1988 |
| DE | 3831278 A1 | 3/1989 |
| DE | 3838011 | 7/1989 |
| DE | 4213426 A1 | 10/1992 |
| DE | 4225112 | 12/1993 |
| DE | 4233978 C1 | 4/1994 |
| DE | 19715202 | 10/1998 |
| DE | 19751761 | 10/1998 |
| DE | 19832296 | 2/1999 |
| DE | 19747427 | 5/1999 |
| DE | 10085137 | 11/2002 |
| EP | 0062941 | 10/1982 |
| EP | 0119660 | 9/1984 |
| EP | 0155857 | 9/1985 |
| EP | 0319844 | 6/1989 |
| EP | 0326768 | 8/1989 |
| EP | 350996 A1 | 1/1990 |
| EP | 0419729 A1 | 4/1991 |
| EP | 0427358 | 5/1991 |
| EP | 0456103 | 11/1991 |
| EP | 0469966 A1 | 2/1992 |
| EP | 0581704 | 2/1994 |
| EP | 0651968 | 5/1995 |
| EP | 0655138 | 5/1995 |
| EP | 0894473 A2 | 2/1999 |
| EP | 0908146 | 4/1999 |
| EP | 0930046 | 7/1999 |
| FR | 2417970 | 9/1979 |
| FR | 2618211 A1 | 1/1989 |
| GB | 2094590 A | 9/1982 |
| GB | 2164856 A | 4/1986 |
| JP | 62327 | 1/1983 |
| JP | 2765738 | 6/1988 |
| JP | 63240851 | 10/1988 |
| JP | 3267054 | 11/1991 |
| JP | 6194639 | 7/1994 |
| WO | WO-8809151 | 12/1988 |
| WO | WO-8905123 | 6/1989 |
| WO | WO-9005494 A1 | 5/1990 |
| WO | WO-9103982 A1 | 4/1991 |
| WO | WO-9104711 | 4/1991 |
| WO | WO-9107726 | 5/1991 |
| WO | WO-9203090 | 3/1992 |
| WO | WO-9206645 | 4/1992 |
| WO | WO-9404938 A1 | 3/1994 |
| WO | WO-9423647 | 10/1994 |
| WO | WO-9424933 A1 | 11/1994 |
| WO | WO-9507055 A1 | 3/1995 |
| WO | WO-9611624 A2 | 4/1996 |
| WO | WO-9632059 A1 | 10/1996 |
| WO | WO-9736192 A1 | 10/1997 |
| WO | WO-9749453 A1 | 12/1997 |
| WO | WO-9808554 A1 | 3/1998 |
| WO | WO-9838908 | 9/1998 |
| WO | WO-9915097 A2 | 4/1999 |
| WO | WO-9921498 A1 | 5/1999 |
| WO | WO-9923956 A1 | 5/1999 |
| WO | WO-9926549 A1 | 6/1999 |
| WO | WO-9927839 A2 | 6/1999 |
| WO | WO-9929253 A1 | 6/1999 |
| WO | WO-9933406 A1 | 7/1999 |
| WO | WO-9937208 A1 | 7/1999 |
| WO | WO-9938449 A1 | 8/1999 |

(56) References Cited

FOREIGN PATENT DOCUMENTS

| WO | WO-9952094 A1 | 10/1999 |
|----|---------------|---------|
| WO | WO-9960939 A1 | 12/1999 |
| WO | WO-0130437 A1 | 5/2001 |

OTHER PUBLICATIONS

"TREON, StealthStation," brochure, Medtronic Surgical Navigation Technologies (2001) 8 pages.
Adams et al., "Orientation Aid for Head and Neck Surgeons," Innov. Tech. Biol. Med., vol. 13, No. 4, 1992, pp. 409-424.
Barrick et al., "Prophylactic Intramedullary Fixation of the Tibia for Stress Fracture in a Professional Athlete," Journal of Orthopaedic Trauma, vol. 6, No. 2, pp. 241-244 (1992).
Barrick et al., "Technical Difficulties with the Brooker-Wills Nail in Acute Fractures of the Femur," Journal of Orthopaedic Trauma, vol. 4, No. 2, pp. 144-150 (1990).
Barrick, "Distal Locking Screw Insertion Using a Cannulated Drill Bit: Technical Note," Journal of Orthopaedic Trauma, vol. 7, No. 3, 1993, pp. 248-251.
Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.
Benzel et al., "Magnetic Source Imaging: a Review of the Magnes System of Biomagnetic Technologies Incorporated," Neurosurgery, vol. 33, No. 2 (Aug. 1993), pp. 252-259.
Bergstrom et al. Stereotaxic Computed Tomography, Am. J. Roentgenol, vol. 127 pp. 167-170 (1976).
Bouazza-Marouf et al.; "Robotic-Assisted Internal Fixation of Femoral Fractures", IMECHE., pp. 51-58 (1995).
Brack et al., "Accurate X-ray Based Navigation in Computer-Assisted Orthopedic Surgery," CAR '98, pp. 716-722.
Klimek, L., et al., Long-Term Experience with Different Types of Localization Systems in Skull-Base Surgery, Ear, Nose & Throat Surgery, Chapter 51, (1996) pp. 635-638.
Kosugi, Y., et al., An Articulated Neurosurgical Navigation System Using MRI and CT Images, IEEE Trans. on Biomed, Eng. vol. 35, No. 2, pp. 147-152 (Feb. 1988).
Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).
Kwoh, Y.S., Ph.D., et al., A New Computerized Tomographic-Aided Robotic Stereotaxis System, Robotics Age, vol. 7, No. 6, pp. 17-22 (Jun. 1985).
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavallee et al, "Matching 3-D Smooth Surfaces with their 2-D Projections using 3-D Distance Maps," SPIE, vol. 1570, Geometric Methods in Computer Vision, 1991, pp. 322-336.
Lavallee et al., "Computer Assisted Driving of a Needle into the Brain," Proceedings of the International Symposium CAR '89, Computer Assisted Radiology, 1989, pp. 416-420.
Lavallee et al., "Computer Assisted Interventionist Imaging: The Instance of Stereotactic Brain Surgery," North-Holland MEDINFO 89, Part 1, 1989, pp. 613-617.
Lavallee et al., "Computer Assisted Spine Surgery: A Technique for Accurate Transpedicular Screw Fixation Using CT Data and a 3-D Optical Localizer," TIMC, Faculte de Medecine de Grenoble. (1995).
Lavallee et al., "Image guided operating robot: a clinical application in stereotactic neurosurgery," Proceedings of the 1992 IEEE International Conference on Robotics and Automation, May 1992, pp. 618-624.
Lavallee et al., "Matching of Medical Images for Computed and Robot Assisted Surgery," IEEE EMBS, Orlando, 1991.
Lavallee, "A New System for Computer Assisted Neurosurgery," IEEE Engineering in Medicine & Biology Society 11th Annual International Conference, 1989, pp. 0926-0927.
Lavallee, "VI Adaption de la Methodologie a Quelques Applications Cliniques," Chapitre VI, pp. 133-148.
Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).
Lavallee, S., et al., Computer Assisted Medical Interventions, NATO ASI Series, vol. F 60, 3d Imaging in Medic., pp. 301-312 (1990).
Leavitt, D.D., et al., Dynamic Field Shaping to Optimize Stereotactic Radiosurgery, I.J. Rad. Onc. Biol. Physc., vol. 21, pp. 1247-1255 (1991).
Leksell et al., "Stereotaxis and Tomography—A Technical Note," ACTA Neurochirurgica, vol. 52, 1980, pp. 1-7.
Lemieux et al., "A Patient-to-Computed-Tomography Image Registration Method Based on Digitally Reconstructed Radiographs," Med. Phys. 21 (11), Nov. 1994, pp. 1749-1760.
Levin et al., "The Brain: Integrated Three-dimensional Display of MR and PET Images," Radiology, vol. 172, No. 3, Sep. 1989, pp. 783-789.
Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).
Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.
Mazier et al., Chirurgie de la Colonne Vertebrale Assistee par Ordinateur: Appication au Vissage Pediculaire, lnnov. Tech. Biol. Med., vol. 11, No. 5, 1990, pp. 559-566.
McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).
Merloz, et al., "Computer Assisted Spine Surgery", Clinical Assisted Spine Surgery, No. 337, (1997) pp. 86-96.
Ng, W.S. et al., Robotic Surgery—A First-Hand Experience in Transurethral Resection of the Prostate Surgery, IEEE Eng. in Med. and Biology, pp. 120-125 (Mar. 1993).
Partial European Search Report mailed Jan. 12, 2005 for EP04024457, claiming benefit of U.S. Appl. No. 10/687,539, filed Oct. 16, 2003.
Pelizzari et al., "Accurate Three-Dimensional Registration of CT, PET, and/or MR Images of the Brain," Journal of Computer Assisted Tomography, Jan./Feb. 1989, pp. 20-26.
Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).
Pelizzari et al., No. 528—"Three Dimensional Correlation of PET, CT and MRI Images," The Journal of Nuclear Medicine, vol. 28, No. 4, Apr. 1987, p. 682.
Penn, R.D., et al., Stereotactic Surgery with Image Processing of Computerized Tomographic Scans, Neurosurgery, vol. 3, No. 2, pp. 157-163 (Sep.-Oct. 1978).
Phillips et al., "Image Guided Orthopaedic Surgery Design and Analysis," Trans Inst. MC, vol. 17, No. 5, 1995, pp. 251-264.
Pixsys, 3-D Digitizing Accessories, by Pixsys (marketing brochure)(undated) (2 pages).
Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.
Reinhardt et al., "CT-Guided 'Real Time' Stereotaxy," ACTA Neurochirurgica, 1989.
Reinhardt, H., et al., A Computer-Assisted Device for Intraoperative CT-Correlated Localization of Brain Tumors, pp. 51-58 (1988).
Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).
Reinhardt, H.F., et al., Mikrochirurgische Entfernung tiefliegender Gefäßmißbildungen mit Hilfe der Sonar-Stereometrie (Microsurgi-

(56) References Cited

OTHER PUBLICATIONS cal Removal of Deep-Seated Vascular Malformations Using Sonar Stereometry). Ultraschall in Med. 12, pp. 80-83 (1991).
Reinhardt, Hans. F., Neuronavigation: A Ten-Year Review, Neurosurgery, (1996) pp. 329-341.
Roberts et al., "A frameless stereotaxic integration of computerized tomographic imaging and the operating microscope," J. Neurosurg., vol. 65, Oct. 1986, pp. 545-549.
Rosenbaum et al., "Computerized Tomography Guided Stereotaxis: A New Approach," Applied Neurophysiology, vol. 43, No. 3-5, 1980, pp. 172-173.
Sautot, "Vissage Pediculaire Assiste Par Ordinateur," Sep. 20, 1994.
Schueler et al., "Correction of Image Intensifier Distortion for Three-Dimensional X-Ray Angiography," SPIE Medical Imaging 1995, vol. 2432, pp. 272-279.
Selvik et al., "A Roentgen Stereophotogrammetric System," Acta Radiologica Diagnosis, 1983, pp. 343-352.
Shelden et al., "Development of a computerized microsteroetaxic method for localization and removal of minute CNS lesions under direct 3-D vision," J. Neurosurg., vol. 52, 1980, pp. 21-27.
Simon, D.A., Accuracy Validation in Image-Guided Orthopaedic Surgery, Second Annual Intl. Symp. on Med. Rob. an Comp-Assisted surgery, MRCAS (1995) pp. 185-192.
Smith et al., "Computer Methods for Improved Diagnostic Image Display Applied to Stereotactic Neurosurgery," Automedical, vol. 14, 1992, pp. 371-382 (4 unnumbered pages).
Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.
Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).
Tan, K., Ph.D., et al., A frameless stereotactic approach to neurosurgical planning based on retrospective patient-image registration, J Neurosurgy, vol. 79, pp. 296-303 (Aug. 1993).
The Laitinen Stereotactic System, E2-E6.
Thompson, et al., A System for Anatomical and Functional Mapping of the Human Thalamus, Computers and Biomedical Research, vol. 10, pp. 9-24 (1977).
Trobaugh, J.W., et al., Frameless Stereotactic Ultrasonography: Method and Applications, Computerized Medical Imaging and Graphics, vol. 18, No. 4, pp. 235-246 (1994).
Viant et al., "A Computer Assisted Orthopaedic System for Distal Locking of Intramedullary Nails," Proc. of MediMEC '95, Bristol, 1995, pp. 86-91.
Von Hanwhr et al., Foreword, Computerized Medical Imaging and Graphics, vol. 18, No. 4, pp. 225-228, (Jul.-Aug. 1994).
Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).
Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.
Watanabe, "Neuronavigator," Igaku-no-Ayumi, vol. 137, No. 6, May 10, 1986, pp. 1-4.
Brown, R., M.D., A Stereotactic Head Frame for Use with CT Body Scanners, Investigative Radiology © J.B. Lippincott Company, pp. 300-304 (Jul.-Aug. 1979).
Bryan, "Bryan Cervical Disc System Single Level Surgical Technique", Spinal Dynamics, 2002, pp. 1-33.
Bucholz et al., "Variables affecting the accuracy of stereotactic localizationusing computerized tomography," Journal of Neurosurgery, vol. 79, Nov. 1993, pp. 667-673.
Bucholz, R.D., et al. Image-guided surgical techniques for infections and trauma of the central nervous system, Neurosurg. Clinics of N.A., vol. 7, No. 2, pp. 187-200 (1996).
Bucholz, R.D., et al., A Comparison of Sonic Digitizers Versus Light Emitting Diode-Based Localization, Interactive Image-Guided Neurosurgery, Chapter 16, pp. 179-200 (1993).
Bucholz, R.D., et al., Intraoperative localization using a three dimensional optical digitizer, SPIE—The Intl. Soc. for Opt. Eng., vol. 1894, pp. 312-322 (Jan. 17-19, 1993).
Bucholz, R.D., et al., Intraoperative Ultrasonic Brain Shift Monitor and Analysis, Stealth Station Marketing Brochure (2 pages) (undated).
Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).
Champleboux et al., "Accurate Calibration of Cameras and Range Imaging Sensors: the NPBS Method," IEEE International Conference on Robotics and Automation, Nice, France, May, 1992.
Champleboux, "Utilisation de Fonctions Splines pour la Mise au Point D'un Capteur Tridimensionnel sans Contact," Quelques Applications Medicales, Jul. 1991.
Cinquin et al., "Computer Assisted Medical Interventions," IEEE Engineering in Medicine and Biology, May/Jun. 1995, pp. 254-263.
Cinquin et al., "Computer Assisted Medical Interventions," International Advanced Robotics Programme, Sep. 1989, pp. 63-65.
Clarysse et al., "A Computer-Assisted System for 3-D Frameless Localization in Stereotaxic MRI," IEEE Transactions on Medical Imaging, vol. 10, No. 4, Dec. 1991, pp. 523-529.
Co-pending U.S. Appl. No. 10/644,680, filed Aug. 20, 2003 entitled "Method and Apparatus for Performing 2D to 3D Registration". cited by other.
Cutting M.D. et al., Optical Tracking of Bone Fragments During Craniofacial Surgery, Second Annual International Symposium on Medical Robotics and Computer Assisted Surgery, pp. 221-225, (Nov. 1995).
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics," The Systems Programming Series, Chapter 7, Jul. 1984, pp. 245-266.
Foley et al., "Image-guided Intraoperative Spinal Localization," Intraoperative Neuroprotection, Chapter 19, 1996, pp. 325-340.
Foley, "The StealthStation: Three-Dimensional Image-Interactive Guidance for the Spine Surgeon," Spinal Frontiers, Apr. 1996, pp. 7-9.
Friets, E.M., et al. A Frameless Stereotaxic Operating Microscope for Neurosurgery, IEEE Trans. on Biomed. Eng., vol. 36, No. 6, pp. 608-617 (Jul. 1989).
Gallen, C.C., et al., Intracranial Neurosurgery Guided by Functional Imaging, Surg. Neurol., vol. 42, pp. 523-530 (1994).
Galloway, R.L., et al., Interactive Image-Guided Neurosurgery, IEEE Trans. on Biomed. Eng., vol. 89, No. 12, pp. 1226-1231 (1992).
Galloway, R.L., Jr. et al, Optical localization for interactive, image-guided neurosurgery, SPIE, vol. 2164, (May 1, 1994) pp. 137-145.
Germano, "Instrumentation, Technique and Technology", Neurosurgery, vol. 37, No. 2, Aug., 1995, pp. 348-350.
Gildenberg et al., "Calculation of Stereotactic Coordinates from the Computed Tomographic Scan," Neurosurgery, vol. 10, No. 5, May 1982, pp. 580-586.
Gomez, C.R., et al., Transcranial Doppler Ultrasound Following Closed Head Injury: Vasospasm or Vasoparalysis?, Surg. Neurol., vol. 35, pp. 30-35 (1991).
Gonzalez, "Digital Image Fundamentals," Digital Image Processing, Second Edition, 1987, pp. 52-54.
Gottesfeld Brown et al., "Registration of Planar Film Radiographs with Computer Tomography," Proceedings of MMBIA, Jun. 1996, pp. 42-51.
Grimson, W.E.L., An Automatic Registration Method for Frameless Stereotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).

(56) References Cited

OTHER PUBLICATIONS

Gueziec et al., "Registration of Computed Tomography Data to a Surgical Robot Using Fluoroscopy: A Feasibility Study," Computer Science/Mathematics, Sep. 27, 1996, 6 pages.

Guthrie, B.L., Graphic-Interactive Cranial Surgery: The Operating Arm System, Handbook of Stereotaxy Using the CRW Apparatus, Chapter 13, (1994) pp. 193-211.

Hamadeh et al, "Kinematic Study of Lumbar Spine Using Functional Radiographies and 3D/2D Registration," TIMC UMR 5525-IMAG (1997).

Hamadeh et al., "Automated 3-Dimensional Computed Tomographic and Fluorscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Hatch, "Reference-Display System for the Integration of CT Scanning and the Operating Microscope," Thesis, Thayer School of Engineering, Oct. 1984, pp. 1-189.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Homer et al., "A Comparison of CT-Stereotaxic Brain Biopsy Techniques," Investigative Radiology, Sep.-Oct. 1984, pp. 367-373.

Hounsfield, "Computerized transverse axial scanning (tomography): Part 1. Description of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly et al., "Computer-assisted stereotaxic laser resection of intraaxial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., Computer-Directed Stereotactic Resection of Brain Tumors, Neurologica Operative Atlas, vol. 1, No. 4, pp. 299-313 (1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images," (1997) pp. 119-128.

\* cited by examiner

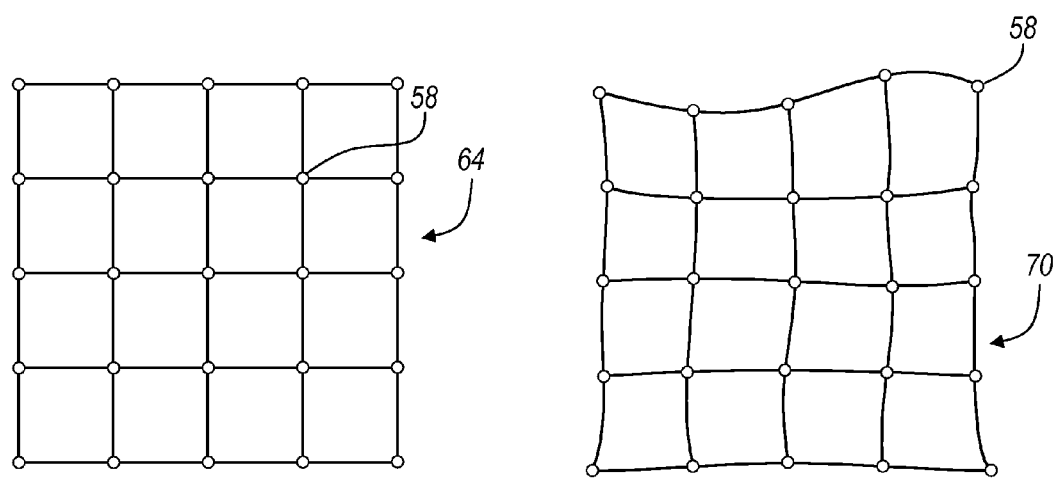
FIGURE 2A
FIGURE 2B
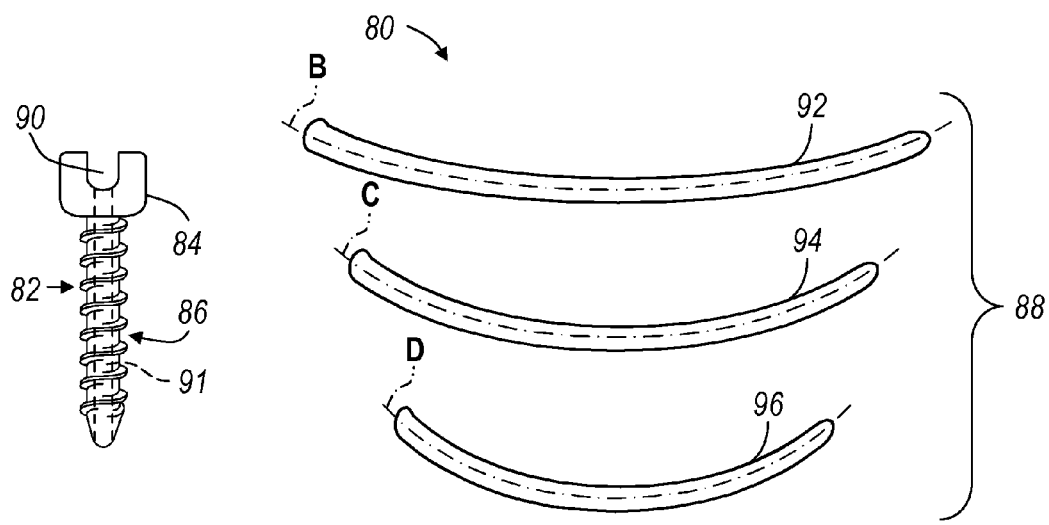
FIGURE 3A

METHOD AND APPARATUS FOR SURGICAL NAVIGATION OF A MULTIPLE PIECE CONSTRUCT FOR IMPLANTATION

CROSS-REFERENCE TO RELATED APPLICATIONS

This application is a continuation of U.S. patent application Ser. No. 10/687,539 filed on Oct. 16, 2003, is now U.S. Pat. No. 7,835,778. The entire disclosure of the above application is incorporated herein by reference.

FIELD

The present invention relates to surgical navigation for assembly and implantation of a multi-piece construct into an anatomy; and particularly to a method and apparatus for percutaneous and/or minimally invasive implantation of constructs into a selected portion of an anatomy.

BACKGROUND

Image guided medical and surgical procedures utilize patient images obtained prior to or during a medical procedure to guide a physician performing the procedure. Recent advances in imaging technology, especially in imaging technologies that produce highly-detailed, two, three, and four dimensional images, such as computed tomography (CT), magnetic resonance imaging (MRI), fluoroscopic imaging, positron emission tomography (PET), and ultrasound imaging (US) has increased the interest in image guided medical procedures.

Image guided surgical techniques have been used to assist surgeons and individuals in various surgical procedures. Various image based navigation systems include U.S. Pat. No. 6,470,207, entitled "Navigational Guidance Via Computer-Assisted Fluoroscopic Imaging", issued Oct. 22, 2002, which is hereby incorporated by reference in its entirety; and image based systems such as the STEALTHSTATION, and various improvements such as the TREON and ION sold by Medtronic Surgical Navigation Technologies of Louisville, Colo. Generally, the procedures and instruments used with image guided surgery allow for visualization or virtual visualization of surgical instruments and various anatomical portions in relation to preacquired or real-time images. Representations of the instruments and implants are generally super-imposed over the preacquired or real-time images of the patients anatomy. Nevertheless, these systems generally require registration of the image data to the patient such that the image data used to guide the procedure matches the patient's intra-operative orientation known as patient space.

Various medical procedures may benefit from image-based navigation systems. For example, a spinal fusion procedure may be performed according to various known techniques. For example, an image based navigation system, such as those discussed above, may be used to assist in a spinal fusion procedure. Nevertheless, the navigation system generally requires the acquisition of a patient image and a registration of the patient image with the surgical patient space to ensure proper guiding and navigation of the instruments and implant portions. Therefore, the image based navigation systems require use of various image acquisition components in an operative procedure, such as the fluoroscopic device, a magnetic resonance imaging (MRI) device, or other image capturing devices. These images are then registered relative to the patient, generally using known registration techniques, such as automatic registration, user guided registration, 2D or 3D registration, point registration and surface registration. Dynamic referencing may also be used to track patient movement during the procedure.

In the alternative, a substantially open procedure may be used to perform the spinal fusion, or anterior cruciate ligament replacement, acetabular implantation, femoral implantation, spinal disc nuclease replacement, spinal disc replacement, and the like. For example, the soft tissue surrounding the spine, particularly a posterior portion of the spine, may be substantially opened or removed such that an "open" view of the spine may be obtained. After the soft tissue has been opened to create the operative passage, the procedure may continue with the user, such as a surgeon, having a clear view of the surgical area. Nevertheless, the open procedures require a large incision and movement of soft tissue. This large incision, movement of soft tissue, and necessary closures, often may require an extended recovery.

Open procedures may also be supplemented with various systems, such as a device to mechanically customize connecting rods by MEDIVISION of Germany. This system may allow for bending of connecting rods to fix a selected geometry. The selected geometry may be determined using any appropriate mechanism, such as a coordinated system or registration system to determine the appropriate angle and shape of the rod.

Alternatively, a substantially percutaneous and/or minimally invasive procedure may be used to position a construct to perform a spinal fusion. During the percutaneous procedure, the various components of the construct are mechanically interconnected or held with an alignment instrument. For example, a head of a pedicle screw may be aligned with such an instrument. Once aligned, the instrument mechanically guides a connector member to interconnect with each pedicle screw.

Although this may be achieved with little difficulty when a low or single level construct, such as a low number of elements are used, such as interconnecting two pedicle screws, it becomes more difficult when attempting to interconnect multi-level constructs, such as more than two pedicle screws. In addition, if the screws are implanted in a selected non-aligned position, such as required by various procedures, the interconnection by a connector is also difficult because the alignment by mechanical means becomes more complex and difficult to achieve. Further, having a constrained geometry increases the complexity. A constrained geometry requires the precise alignment of a plurality of portions that is complex in a percutaneous procedure using mechanical interconnections for alignment.

Therefore, it is desirable to provide a method and apparatus for performing surgical navigation of a percutaneous procedure to implant a selected construct. It is also desirable to provide a surgical navigation apparatus and method for generally planning and confirming an assembly of a construct percutaneously to substantially minimize or reduce trauma to the soft tissue and reduce the size of the incisions required to access the anatomical portions. It is also desirable to perform an imageless surgical navigation procedure that does not require registration of image data with patient space.

SUMMARY

A method and apparatus for providing a selected multi-component construct relative to other components or to a selected portion of an anatomy. Generally, the apparatii include instruments or elements that can be localized by being sensed or detected with various instruments. For example, optical or electromagnetic (EM) localization techniques may be used to determine the precise location of a selected implant construct or implantation instrument. For example, an optical localizer can be positioned relative to an extender extending from implant element, such as a screw. Similarly, a coil may be positioned in an EM field such that the position of the coil may be determined by sensing the induced voltage, and vice versa.

In addition, the apparatii, such as a computer, may allow for the selection of various components that can be implanted to form the selected construct. For example, a predetermined or selected outcome can be used to provide or form a selected construct from various components such that the selected outcome may be achieved. The various instruments may be used to plan and select intraoperatively the various portions of the construct that may be positioned relative to the anatomy.

In addition, the various instruments may be used to guide and track the various portions of the construct to ensure that the selected plan is achieved. Therefore, a plan may be formulated prior to the implantation of at least all of the construct to ensure the achievement of the selected outcome. The actual procedure may be performed using the selected plan and the procedure may be monitored, tracked, and navigated to ensure that the selected outcome is achieved. The whole process may be performed in an imageless manner and, thereby, without a need to register images with the patient space.

According to various embodiments a system for use in navigating an implantation of a selected construct is disclosed. The system includes a first member and a second member of the construct adapted to selectively interact with each other after implantation. A localization element is selectively associated with at least one of the first member and the second member. A detector is able to detect the localization element when the localization element is associated with at least one of the first member and the second member. Also, a processor is operable to assist in navigation of the second member relative to the first member. The processor is operable to receive position information for at least one of the first member and the second member from the detector and further operable to determine a relative position of the other of the at least one of the first member and the second member. The relative position is operable to allow a navigation of at least one of the first member and the second member.

According to various embodiments a system for use in determining a position of a first implantable member and planning and navigating relative to the first member for positioning a second member to interact with the first member is disclosed. The system includes a tracking element associated with the first member to assist in determining a position of the first member. A first detector detects the tracking element and a processor determines a position of the first member depending upon the detection of the first detector. A navigable instrument is operable to move the second member relative to the first member; and a second detector detects the navigable instrument. The processor is operable to determine a position of the second member relative to the first member in at least two planes. The processor is operable to navigate the navigable instrument relative to the tracking element for positioning of the second member relative to the first member.

According to various embodiments a method of percutaneous and/or minimally invasive implantation of a construct having at least a first member, a second member, and a third member is disclosed. The method includes positioning the first member and determining a position of the first member in a selected space. The method further includes positioning the second member relative to the first member and determining a position of the second member in the selected space. Also, navigating the third member relative to the first member and the second member may be performed. The navigation generally includes determining a real time optimal position of the third member in the selected space; and determining a real time position of the third member relative to at least one of the first member and the second member.

According to various embodiments is also disclosed a method of implanting a construct of at least a first member, a second member, and a third member substantially percutaneously and/or minimally invasive. The method includes selecting a final orientation of at least one of the first member, the second member, and the third member relative to at least one other of the first member, the second member, and the third member. A determination of the position of the first member and the second member and displaying the position of each of the first member and the second member is also performed. A characteristic of at least one of the first member, the second member, and the third member is selected. Also, positioning with navigation at least one of the first member, the second member, and the third member relative to another of at least one of the first member, the second member, and the third member to achieve the selected final orientation.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2A is an ideal calibration image for the optional imaging system;

FIG. 2B is a non-ideal calibration image for the optional imaging system;

FIG. 3A is a construct according to an embodiment;

DETAILED DESCRIPTION OF VARIOUS EMBODIMENTS

The following description of various embodiments is merely exemplary in nature and is in no way intended to limit the invention, its application, or uses. Although the following description relates generally to the placement of screws, such as pedicle screws, and a member or connector relative to the pedicle screws in a spinal procedure, it will be understood that the apparatus and methods may be used for other procedures without departing from the scope of the present description and appended claims. For example, while pedicle screws may be implanted relative to a pedicle in a vertebrae, various other screws may be implanted relative to other bone portions that may also be tracked and navigated using instruments and devices as disclosed herein. In addition, other implants, such as multi-component implants that require positioning of one component relative to another component may be implanted according to selected constructs using instruments and methods similar to those described herein. These implants may include joint implant, soft tissue implant, such as ligament implants, tendon implants and spinal disc implants, and others.

Furthermore, the procedure may occur in any appropriate manner. For example, the procedure may be substantially open, or percutaneously or minimally invasively. Therefore, it will be understood that the description of the procedure is not intended to be limited to any particular form of a procedure. In addition a percutaneous and a minimally invasive procedure may be similar in regarding the small size of incisions, when compared to open procedures, to perform the procedure. Generally, a percutaneous and/or minimally invasive procedure includes a substantially small incision such that a portion of the operative site is covered by dermis tissue and dermis tissue healing time is reduced. Although an open procedure may also be percutaneous as occurring generally through the skin and generally include a puncture wound.

Figure 1:
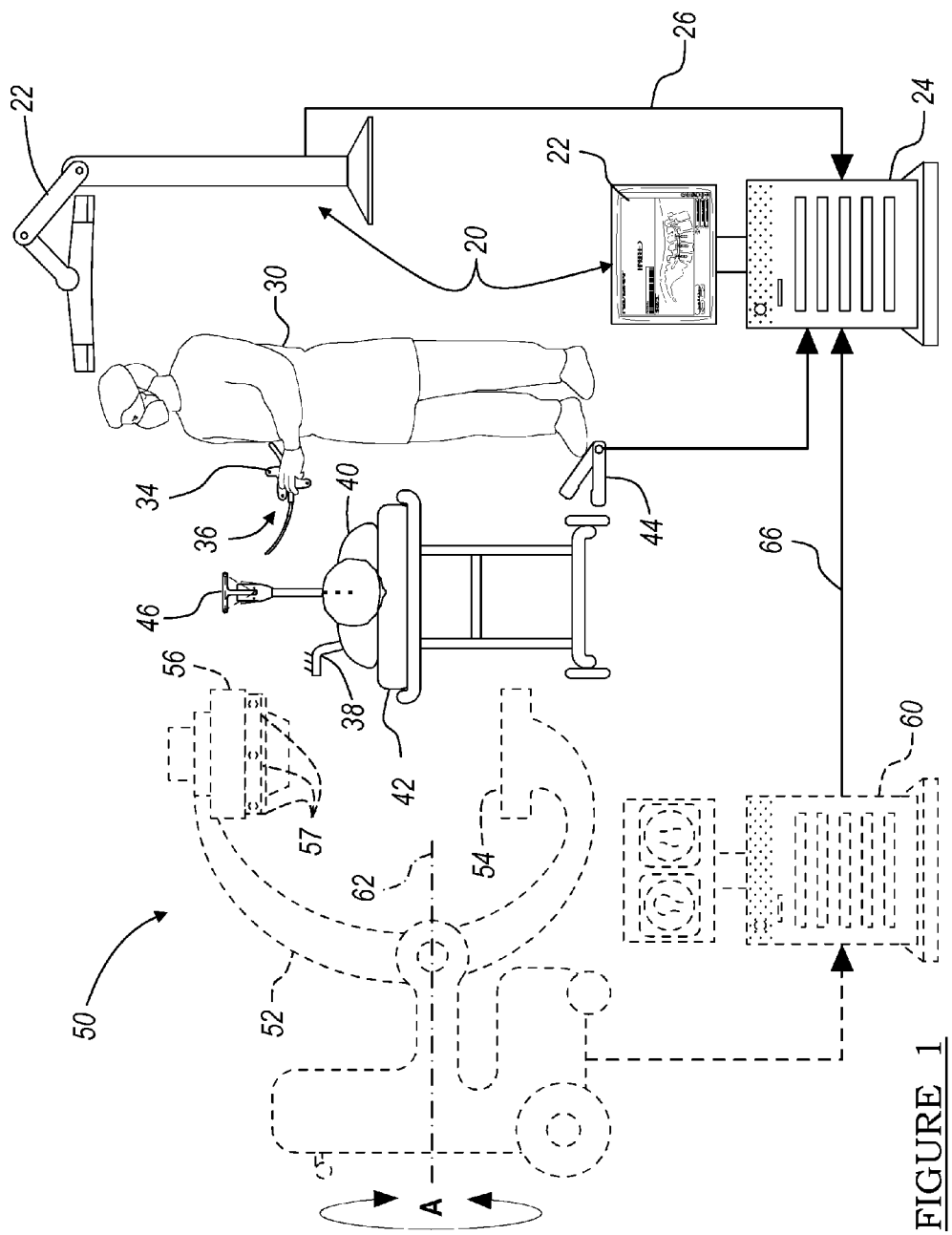
FIG. 1 is an environmental view of a surgical navigation system including an optional imaging system.

With reference to FIG. 1, a surgical navigation system 20, which may include any appropriate surgical navigation system, is illustrated. For example, the surgical navigation system 20 may include an optical navigation system, an electromagnetic navigation system, and acoustic navigation system, an ultrasound, or any other appropriate navigation system.

Although the following discussion generally relates to the use of an optical navigation system, it will be understood that any appropriate navigation system may be used and the optical navigation system is described merely as an example. Exemplary electromagnetic navigation systems are set out in U.S. Pat. No. 6,493,573, issued Dec. 10, 2002, entitled "METHOD AND SYSTEM FOR NAVIGATING A CATHETER PROBE IN THE PRESENCE OF FIELD-INFLUENCING OBJECTS"; U.S. Pat. No. 5,592,939, issued Jan. 14, 1997, entitled "METHOD AND SYSTEM FOR NAVIGATING A CATHETER PROBE; U.S. Pat. No. 6,516,212, issued Feb. 4, 2003, entitled "THREE DIMENSIONAL MAPPING"; U.S. Pat. No. 6,522,907, issued Feb. 18, 2003, entitled "SURGICAL NAVIGATION"; each of which is incorporated herein by reference.

The surgical navigation system 20 generally includes an optical detector 22 operably connected to a computer or processor 24 through an appropriate communication line 26. The detector 22 may also include a plurality of detector. Each of the plurality of detectors may be able to detect a different source, such as EM or optical. Therefore, the navigation system 20 may be able to detect more than one tracking element. The line 26 may be any appropriate line and may also be a wireless connection. Therefore, the detector 22 may be positioned anywhere relative to the navigation computer 24 and communicates therewith over the line 26. In addition, a monitor or display 28 may be provided for a user to view, such as a surgeon 30. The monitor 28 may be any appropriate monitor and may also include a heads-up or head mounted display. Nevertheless, it will be understood that the monitor 28 is able to display an image produced by the computer 24 based upon a preset program or user input according to the teachings of the present invention.

The detector 22 may be operably located in any appropriate location such that the detector 22 is able to detect a tracking element 34 operably connected to a selected instrument 36. The detector 22 may also be operable to detect any other appropriate tracking element. For example, the detector 22 may also be able to detect an optional dynamic tracking reference element 38. As discussed herein, however, the dynamic tracking element 38 may not be necessary depending upon the selected parameters for the surgical navigation system 20, the procedure being performed, user preference, and other appropriate considerations, further discussed herein. Nevertheless, if the dynamic reference tracking element 38 is selected to be used, the dynamic tracking reference 38 is generally affixed to a patient 40. The patient 40 is generally positioned on a selected platform or operating room (OR) table 42 for the procedure.

The tracking element 34 may include any appropriate tracking portion, that may depend on the various navigation systems. Various examples include a tracking element selected from a group including an electromagnetic tracking device, an optical tracking device, a conductive tracking device, a fiberoptic tracking device, an acoustic tracking device, and combinations thereof. Similarly the detector may be formed to detected any of these tracking elements.

According to various embodiments an optical navigation system includes the tracking element 34 that may include a selected number of reflectors to reflect a light source or a light source, such as light emitting diodes (LEDs). The detector 22 is able to detect the light emitted to determine a position of the tracking element. In other systems, such as electromagnetic systems, a coil may either transmit a field or detect a field to determine a location. The EM systems may help eliminate issues such as line of sight, such as when an opaque object blocks the path of the light from the tracking element 34.

During the procedure, the user 30 may use any appropriate input device 44, element such as a foot pedal, to input a selected input into the navigation computer 24. In addition, the monitor 28 may include a touch screen, or other appropriate mechanisms such as a mouse or computer keyboard as the input device 44. Nevertheless, the navigation system 20 is generally able to navigate and determine a location of the tracking elements. In addition, an implant or secondary dynamic tracking element 46 may also be provided. As discussed herein, the implant tracking element 46 may be interconnected to a selected implant to determine a location of the selected implant after it is implanted into the patient 40. The implant tracking element 46 may also be used to track the implant during any appropriate time such as during implantation, after implantation, or even before implantation for various reasons, such as determining an appropriate implantation position.

Generally, when the detector 22 is an optical detector 22 and the navigation system 20 is an optical navigation system, the detector 22 is able to optically locate the various tracking elements 34, 38 and 46. The location of the tracking elements, may be referenced to any appropriate reference. For example, the tracking elements may be referenced to any position within the detector space, which is the space that is detectable by the detector 22. In addition, the tracking elements 34, 38 and 46 may be referenced to a patient space which is defined by the space or area under which the procedure is being performed relative to the patient 40. In addition, the detector 22 may detect, and the surgical navigation system 20 navigate, the various tracking elements relative to images that may be acquired pre-, intra-, or post operatively. Nevertheless, as discussed herein, the detector 22 is able to locate the various elements according to any appropriate space for navigation by the navigation computer 24 for selected display on the monitor 28. In addition the navigation computer 24 may navigate the selected instruments relative to selected points, such as a position of an implant, further discussed herein.

While the navigation system 20 is used to assemble a construct in an imageless manner (i.e., no patient image is acquired before, during or after the procedure), an optional image acquisition system 50 may also be used, if desired. The optional imaging device 50 may be used to acquire any appropriate pre-operative or real time images of the patient 20. The optional imaging device 50 may be provided to obtain pre-operative imaging, such as magnetic resonance imaging (MRI), fluoroscopic, x-ray, and other appropriate or selected images. If pre-operative images are obtained, the pre-operative images may be used to plan a selected procedure depending upon the data acquired from the pre-operative images. On the day of the procedure, the optional imaging device 50 may also be used to image the patient 40 for any selected purpose.

This image may be used for pre-operative planning, for scaling, morphing, translating or merging atlas maps or 3-D models, and to verify that the construct has been assembled properly. For example, as discussed herein, the atlas map may also be scaled or morphed to the known location, based upon the size and orientation of the implant, such as the screw. Generally, the optional imaging device 50 may be selected from any appropriate imaging device such as a computer aided topography (CT) imaging device or a fluoroscopic x-ray imaging device. If the optional imaging device 50 is a CT device, the patient generally has a series of CT scans taken on the area of interest for the selected procedure. In addition, if the optional imaging device 50 is the fluoroscopic device, a plurality or selected number of fluoroscopic x-ray images may also be taken. The pre-operative and intra-operative or immediate operative images may then be merged or referenced depending upon selected procedures. For example, the pre-operative and intra-operative images may include anatomical landmarks that may be referenced by the navigation computer 24 and used to merge or register one set of the images with another set of images or to register the images to patient space as is known in the art. Various exemplary image fusing systems include those set forth in U.S. patent application Ser. No. 10/644,680, filed Aug. 20, 2003 entitled "Method and Apparatus for Performing 2D to 3D Registration", which is incorporated herein by reference.

Other various image merging techniques may use fiducial markers that may be referenced by both the pre and intra-operative images. In this regard, distinct identifiable fiducial markers may be attached to the patient 40 during the pre-operative scans, such as with the MRI. The fiducial markers are generally identifiable in the MRI image dataset by a user or a selected computer. The fiducial markers are generally not removed from the patient after the pre-operative images are obtained and the data is captured such that they are also visible on the later acquired images, such as with the CT or fluoroscopic image. By using the various common corresponding points of the two image data sets, the pre-operative and the intra-operative datasets can be identified thus allowing merging or registration of the images or registration between the images and patient space. Other image or merging registration techniques include the use of surface contours or anatomical landmarks which can either be manually or automatically identified by the processor 24 to provide various merging and registration options, as is known in the art.

As discussed above, the optional imaging device 50 may include a fluoroscopic x-ray imaging device that may be used in a place of other approximate imaging devices, such as CT imaging. Similar registration techniques may be used to register the pre-acquired image dataset with the later acquired image dataset such as from the fluoroscopic x-ray imaging system and with the patient space. The fluoroscopic x-ray imaging device, if used as the optional imaging device 50, may include a fluoroscopic device 52, having an x-ray source 54, and x-ray receiving section 56, and may include an optional calibration and tracking targets and optional radiation sensors, such as those known in the art. Also a tracking element 57 may be included on the optional imaging device 50, particularly on the receiving section 56. The calibration and tracking target generally includes calibration markers 58 (See FIGS. 2A-2B), further discussed herein. Such optional imaging systems may include those described in U.S. Pat. No. 6,470,207, issued Oct. 22, 2002, entitled "Navigational Guidance Via Computer-Assisted Fluoroscopic Imaging" which is hereby incorporated by reference.

A fluoroscopic device controller 60 captures the x-ray images received at the receiving section 56 and stores the images for later use. The fluoroscopic device controller 60 may also control the rotation of the fluoroscopic device 52. For example, the fluoroscopic device 52 may move in the direction of arrow A or rotate about the long axis of the patient 40, allowing anterior or lateral views of the patient 40 to be imaged. Each of these movements involve rotation about a mechanical axis 62 of the fluoroscopic device 52. In this example, the long axis of the patient 40 is substantially in line with the mechanical axis 62 of the fluoroscopic device 16. This enables the fluoroscopic device 52 to be rotated relative to the patient 40, allowing images of the patient 40 to be taken from multiple directions or about multiple planes. An example of a fluoroscopic device x-ray imaging device 50 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed fluoroscopic device systems, isocentric fluoroscopic device systems, 3D fluoroscopic systems, etc.

In operation, the imaging device 50 generates x-rays from the x-ray source 54 that propagate through the patient 40 and a calibration and/or tracking target 64, into the x-ray receiving section 56. The receiving section 56 generates an image representing the intensities of the received x-rays. Typically, the receiving section 56 includes an image intensifier that first converts the x-rays to visible light and a charge coupled device (CCD) video camera that converts the visible light into digital images. Receiving section 56 may also be a digital device that converts x-rays directly to digital images, thus potentially avoiding distortion introduced by first converting to visible light. With this type of digital, which is generally a flat panel device, the optional calibration and/or tracking target 64 and the calibration process discussed below may be eliminated. Also, the calibration process may be eliminated or not used depending on the type of therapy performed. Alternatively, the imaging device 50 may only take a single image with the calibration and tracking target 64 in place. Thereafter, the calibration and tracking target 64 may be removed from the line-of-sight of the imaging device 50. Again, it should be noted that the imaging device 50 is optional and may be utilized during the selected procedure, such as an implantation procedure, to merely confirm that the instrument has hit the desired target or that the construct has been assembled properly.

Two dimensional fluoroscopic images taken by the imaging device 50 are captured and stored in the fluoroscopic device controller 60 and/or directly within the various navigation or viewing systems. Multiple two-dimensional images taken by the imaging device 50 may also be captured and assembled to provide a larger view or image of a whole region of a patient 40, as opposed to being directed to only a smaller portion or region of the patient 40. For example, multiple image data of the patient's spine may be appended together to provide a full view or complete set of image data of the spine that may be used at a selected time. These images are then forwarded from the fluoroscopic device controller 60 to the controller, navigation computer or work station 24 having the display 28 and the user interface 44. As an example, the navigation computer 24 assembles the various images, but this may also be performed by the controller 60. The data set may be communicated over line 66 that may be a hard line or a wireless communication system. The work station 24 provides facilities for displaying on the display 28, saving, digitally manipulating, or printing a hard copy of the received images from both the imaging device 50 and from pre-operative scans, such as the preoperative MRI scans as discussed herein.

The user interface 44, as discussed above, may be a keyboard, mouse, touch pen, touch screen or other suitable device that allows a physician or user to provide inputs to control the imaging device 50, via the fluoroscopic device controller 60, or adjust the display settings of the display 28. The work station 24 may also direct the fluoroscopic device controller 60 to adjust the rotational axis 62 of the fluoroscopic device 52 to obtain various two-dimensional images along different planes in order to generate representative two-dimensional and three-dimensional images. When the x-ray source 54 generates the x-rays that propagate to the x-ray receiving section 56, the radiation sensors sense the presence of radiation, which is forwarded to the fluoroscopic device controller 60, to identify whether or not the imaging device 50 is actively imaging. Alternatively, a person or physician may manually indicate when the imaging device 50 is actively imaging or this function can be built into the x-ray source 54, x-ray receiving section 56, or the control computer 60.

Fluoroscopic imaging devices 50 that do not include a digital receiving section 56 generally require the optional calibration and/or tracking target 64. This is because the raw images generated by the receiving section 56 tend to suffer from undesirable distortion caused by a number of factors, including inherent image distortion in the image intensifier and external electromagnetic fields. An empty undistorted or ideal image and an empty distorted image are shown in FIGS. 2A and 2B, respectively. The checkerboard shape, shown in FIG. 2A, represents the ideal image 64 of the checkerboard arranged calibration markers 58. The image taken by the receiving section 56, however, can suffer from distortion, as illustrated by the distorted calibration marker image 70, shown in FIG. 2B.

Intrinsic calibration, which is the process of correcting image distortion in a received image and establishing the projective transformation for that image, involves placing the calibration markers 58 in the path of the x-ray, where the calibration markers 58 are opaque or semi-opaque to the x-rays. The calibration markers 58 are rigidly arranged in pre-determined patterns in one or more planes in the path of the x-rays and are visible in the recorded images. Because the true relative position of the calibration markers 58 in the recorded images are known, the c fluoroscopic device controller 60 or the work station or computer 24 is able to calculate an amount of distortion at each pixel in the image (where a pixel is a single point in the image). Accordingly, the computer or work station 24 can digitally compensate for the distortion in the image and generate a distortion-free or at least a distortion improved image 64 (see FIG. 2a).

A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While a fluoroscopic imaging device 50 is shown in FIG. 1, any other alternative 2D, 3D or 4D imaging modality, as already discussed herein, may also be used for preoperative, intraoperative, and postoperative imaging. For example, any 2D, 3D or 4D imaging device, such as fluoroscopic, fluoroscopic isocentric, bi-plane fluoroscopy, ultrasound, computed tomography (CT), multi-slice computed tomography (MSCT), magnetic resonance imaging (MRI), high frequency ultrasound (HIFU), positron emission tomography (PET), optical coherence tomography (OCT), intra-vascular ultrasound (IVUS), ultrasound, intra-operative CT or MRI may also be used to acquire 2D, 3D or 4D pre-operative or real-time images or image data of the patient 40, further discussed herein. The images may also be obtained and displayed in two, three or four dimensions. In more advanced forms, four-dimensional surface rendering of the body may also be achieved by incorporating data from an atlas map or from pre-operative image data captured by MRI, CT, MSCT, HIFU, OCT, PET, etc. A more detailed discussion on optical coherence tomography (OCT), is set forth in U.S. Pat. No. 5,740,808, issued Apr. 21, 1998, entitled "Systems And Methods For Guilding Diagnostic Or Therapeutic Devices In Interior Tissue Regions" which is hereby incorporated by reference.

Regarding the use of atlas mapping, atlas maps may be utilized during the preplanning stage to locate target sites within the spine, or other selected anatomical region, of the patient 40. In this regard, known anatomical atlas maps may be used and scaled to the particular patient 40 or patient specific atlas maps may also be utilized that are updated over time. In this regard, over multiple procedures, enhancements and refinements in the location of certain desired sites within the anatomy may be updated as these procedures are performed, thus providing an atlas map that is updated with each surgical procedure to provide more precise mapping by performing more procedures and gathering additional data. These atlas or patient specific atlas maps may then be superimposed onto optional preacquired images to identify relevant locations of interest. Alternatively, only the atlas models may be used to provide a true imageless system with the advantage of providing the surgeon an anatomical reference during the procedure and without the need to capture images of the patient, further discussed herein Image datasets from hybrid modalities, such as positron emission tomography (PET) combined with CT, or single photon emission computer tomography (SPECT) combined with CT, may also provide functional image data superimposed onto anatomical data to be used to confidently reach target sights within the areas of interest. It should further be noted that the fluoroscopic imaging device 50, as shown in FIG. 1, provides a virtual bi-plane image using a single-head C-arm fluoroscope 50 by simply rotating the C-arm 52 about at least two planes, which could be orthogonal planes to generate two-dimensional images that can be converted to three-dimensional volumetric images. By acquiring images in more than one plane, an icon representing the location of an instrument or lead, introduced and advanced in the patient 40, may be superimposed in more than one view on display 28 allowing simulated bi-plane or even multi-plane views, including two and three-dimensional views, if desired.

With reference to FIG. 3A and additional reference to FIG. 1, a construct 80 that may be implanted in an imageless manner in a spine to rigidly fix relative vertebrae is shown. The first members, however, may be a fastener of any appropriate type. The construct 80 generally includes a plurality of first members or pedicle screws 82 that may be implanted into a selected vertebrae as is known in the art. The screw 82 generally includes a head portion 84 and a threaded portion 86. The threaded portion 86 is generally adapted to threadably engage a selected boney portion and be held therein. The head portion 84 is formed to removably receive a localization element, further described herein and may also be formed to operably engage a connector 88. In this regard the screw 82 includes or defines a slot 90 that is operable to slidably receive the connector 88. Also, the head portion 84 may be moveable or pivotable relative to the threaded portion 86. Thus, the screw 82 may also be a multi-axis screw. The screw 82 may also define a cannula 91 through the screw. Therefore, the screw 82 may be positioned over a guide wire or K-wire that has fitted into a selected position, such as pedicle to assist in positioning the screw 82 thereto. Nevertheless, the screw 82 need not be cannulated and need not include the cannula 91, therefore, the cannula 91 is optional.

The connector 88 is selected from a plurality of connectors having various characteristics, for example a first connector 92, a second connector 94, and a third connector 96. The first connector 92 include a radius or arc B of any appropriate size. In addition, the connector 92 includes a selected length, which also may be varied or numerous. Likewise, the second connector 94 defines a second arc C while the third connector 96 defines a third arc D. Each of the connectors, 92, 94, 96 may define different or same arcs or radii. In addition, each may define a substantially equal length or different lengths and may be provided as a kit with or without the screw 82. Nevertheless, the connector 88 in conjunction with the screws 82 form the construct elements from which the construct 80 may form a spinal implant. It will be understood that the type and number of elements is merely exemplary and any appropriate members may be used to form the construct 80.

Figure 3B:
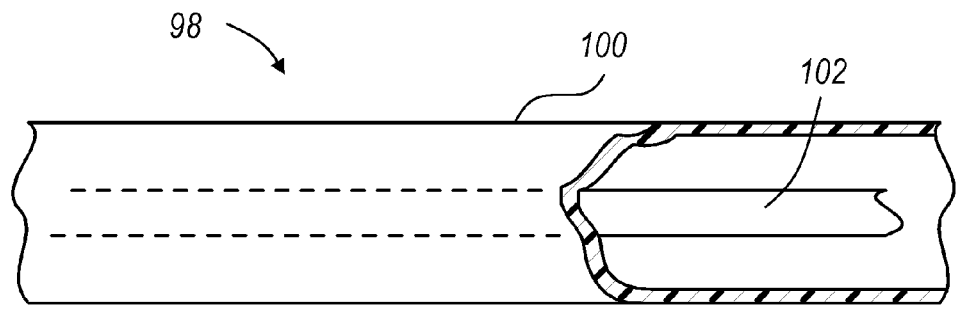
FIG. 3b is a connector for the construct of FIG. 3a according to various embodiments.

In addition, the connectors 88 may or may not be rigid members that rigidly interconnect the screws 82. Regardless, the connector 88 may be selectable in size, shape, orientation, arc, length, and any other appropriate dimension relative to a selected procedure. Also, the connector 88 may be a substantially drivable or steerable element 98. With reference to FIG. 3B, steerable element 98 includes a cover or balloon 100 that may be filled with a selected compound, such as a carbon or bone matrix that may set to form a substantially rigid rod. The steerable connector 98 may also include a substantially steerable or guidable portion 102 that allows the steerable connector 98 to be moved between relative directions. The guidable portion 102 may be selected from but not intended to be a limiting example, from a guided stylet or K-wire that is used to position the balloon 100 in the selected position. The steering member 102 may steer the steerable connector 98 as an assembly and once positioned in the selected position the hardenable or curable material may be used to fill the balloon 100 and allowed to cure to form a substantially rigid connector. Therefore, the connector 88 need not be predetermined, but may be selected during the procedure. Also, the connector 88 need not be rigid nor include a balloon to be filled with a matrix, but may be at least partially deformable such that it may be placed under tension. For example, the connector 88 may be formed as a cord or cable that includes a selected stiffness but may be deflected to provide a selected tension to a selected component, such as an anatomical portion. As described herein, the connector may be navigated to a selected location. Therefore, the connector 88 may also include a tracking element to be detected by the detector 22.

Figures 4A, 4B, 4C:
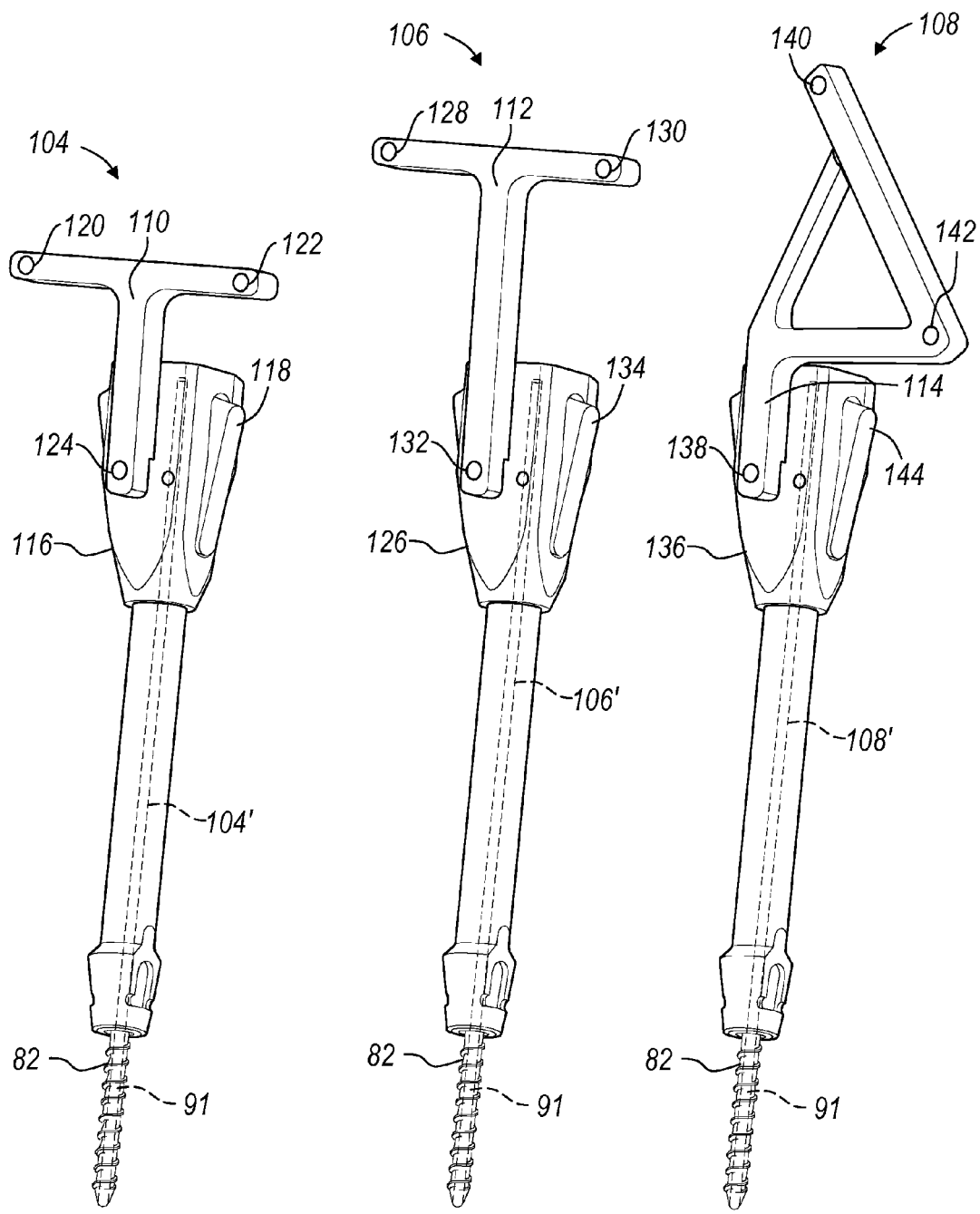
FIGS. 4A-4C are localization units according to various embodiments.

With continuing reference to FIG. 3A and additional reference to FIGS. 4A through 4C, a localization member may be any appropriate localization member, for example a first localization member 104, a second localization member 106, and a third localization member 108. Each localization member includes a tracking element 110, 112, and 114, respectively. Each of the tracking elements 110, 112, and 114 may be detected by the optical detector 22, as described herein. In addition, each of the localization members 104, 106 and 108 may include a cannula 104', 106' and 108', respectively. The cannula 104', 106' and 108' may generally be substantially aligned with the cannula 91 formed in the screw 82, if one is provided. In addition, each of the localization elements 104, 106, and 108 need not be cannulated and are only optionally cannulated to assist in positioning the localization elements 104, 106, and 108 relative to the respective screw 82 and over a guide wire, if used.

With reference to FIG. 4A, the localizer 104 includes the tracking element 110 that is operably affixed to an extender or positioning element 116. The extender 116 generally interconnects with the screw 82 through any appropriate means. For example, the extender 116 may include a depressible member 118 that operates an internal mechanism to engage and disengage the head 84 of the screw 82. Therefore, the extender 116 may be quickly engaged and disengaged percutaneously from the screw 82 at a selected time.

Also, the extender 116 may be keyed relative to a selected shape of the head 84 of the screw 82 or may simply be positioned on the screw 82 to provide a position thereof. If the extender 116 is generally keyed to a position of the screw 82 or a portion of the screw 82, the localization unit 104, or any of the localization elements, may substantially only engage the screw 82 in one selected position and may be used to determine a position, an orientation, and rotational (i.e., six degree of freedom) information. This may assist in determining an orientation of the threaded portion 86 relative to the head 84 when the head 84 is moveable relative to the threaded portion 86. Otherwise, the localization units, 104, 106, and 108 may be selected to provide only a three-dimensional location, generally including the coordinates X, Y and Z, and rotational position of the screw. Generally, the localization units, 104, 106, and 108 are able to determine the center of rotation of the screw such that the known position of the tracking element 110 may allow for a determination of the orientation of the screw.

Alternatively, a multi access screw may include a head or a portion of the head 84 that may be moved randomly relative to a threaded portion or a body 86 of the screw 82. Therefore, rather than having an extender that is keyed to a specific or selected screw, the extender may operably engage the multi access screw to fix the head in a selected position. Therefore, the extender may engage the multi-access screw in a generally known manner to fix the screw in a selected orientation. The extender engages the screw and holds it in the selected orientation such that the orientation of the screw is known due to the attachment of the extender. This allows a determination of an orientation of the screw because the extender has locked the screw in the selected position.

The extender 116 includes a known length or dimension. Similarly, the position of a plurality of tracking points 120 and 122 and 124 are generally known relative to the dimension of the extension 116. Therefore, the detector 22 may detect the tracking points 120, 122, 124 and determine the position of the screw 82 using the information, such as length of the extender 116 stored in the computer 24. Again, the tracking points 120, 122, 124 may be LEDs or reflectors for the optical detector 22, as is known in the art. In the alternative, when the navigation system is an electromagnetic type of system EM coils may be used. In addition, the screw 82 may internally include the selected tracking points, such as EM coils. Therefore, the screws 82 may be detected without attaching the localization element 104 to the screw. It will be understood that any appropriate number of screws may use EM coils as the tracking device or localization elements, thus the localization elements 104, 106, and 108 may not be necessary.

With reference to FIG. 4B, the second localization unit 106 may include an extender 126 that includes a second selected length. Attached to the extender 126 is a tracking element 112 that includes three different tracking points 128, 130 and 132. Again, the extender 126 is generally interconnected with a screw 82 at a selected time. Again, quick release or attachment levers 134 allow for easy and selectable connection to the screw 82. Again, the extender 126 may be keyed or simply connectable to the head 84 of the screw 82. In addition, the third localization element 108, with reference to FIG. 4C, includes an extender 136 may include a tracking element 114 that includes tracking points 138, 140, 142. Again, detachable levers may be provided to interconnect the extender 136 with the screw 82. Also, the extender 136 may include a length different from the extenders 116, 126 and the tracking element 114 may include dimensions or shapes different from the tracking elements 110 and 112.

The navigation computer 24 generally includes a database of the distinct shape of each of the various localization elements 104, 106, and 108 that may be provided for use with the construct 80. Therefore, the extender 116 may be chosen and the use of the extender 116 is selected on the navigation computer 24. In addition, the position of the extender 116 is also noted by the tracking computer 24, generally through an input provided by a user, which may be the physician or an assistant to the physician, such that the detector 22 is able to detect the tracking element 110 and the detector 22 is able to transmit the location of the tracking element 110 to the computer 24. The computer 24 is then able to determine the position of the screw head 84 due to the known length of the extender 116, the orientation and size of the tracking element 110, and therefore display on the monitor 28 an icon representing the position of the screw 82.

Similarly, if the extenders 126 and 136 are used, the preknown or pre-programmed sizes, orientation, and dimensions of the extenders 126, 136 and the relative tracking elements 112, and 114 are also known such that there inputted attachments to a selected screw can be used by the computer 24 to display on the monitor 28 the position of the other screws 82. It will also be understood that a plurality of each of the localization elements 104, 106, and 108 may be used in a selected procedure and programmed into the computer 24 such that the computer 24 is able to know the distinct location of each.

In addition, the various configurations of the tracking elements 110, 112, 114 may be used by the computer 24 to identify each of the respective localization elements, 104, 106, and 108. Therefore, the tracking element 110 may include a geometry different from that of the tracking element 112 such that the computer 24 is able to distinguish the location of each of the localization elements 104, 106, 108. The computer 24 may be preprogrammed with the size of each of the specific localization units 104, 106, 108 depending upon the geometry of the tracking elements such that the computer 24 is able to determine the presence of any of the programmed localization elements 104, 106, 108 and determine the position of the screw 82 relative thereto. It will be understood that although the tracking element 110, 112, 114 is displaced from the screw 82, the position of the screw 82 is known because the extension portion 116, 126, 136 is substantially rigid and does not change over the course of the procedure.

As noted above an EM based navigation system may also be used as opposed to an optical based system. In an exemplary EM based system coils may be positioned in the implanted elements, such as a pedicle screw. The coils embedded in the screw can then be detected, by transmitting or detecting an EM field, to determine the location of the screw. Therefore, although the following discussion relates to the use of an optical system it will be understood that an EM navigation system, or any appropriate navigation system, may be used.

Reference to the dynamic reference frame 38 if selected, or reference to the tracking element of any of the selected localization members 104, 106, 108, may be used by the navigational computer 24 to determine the location of the instrument 36 or any selected element relative to the selected reference. Therefore, any selected reference point may be used to navigate the instrument 36 or any appropriate selected member, such as the connector 88. Although the following discussion relates to referencing a selected implant and the localization member affixed thereto, it will understood that reference may be made to any selected tracking element or selected portion.

Figure 5:
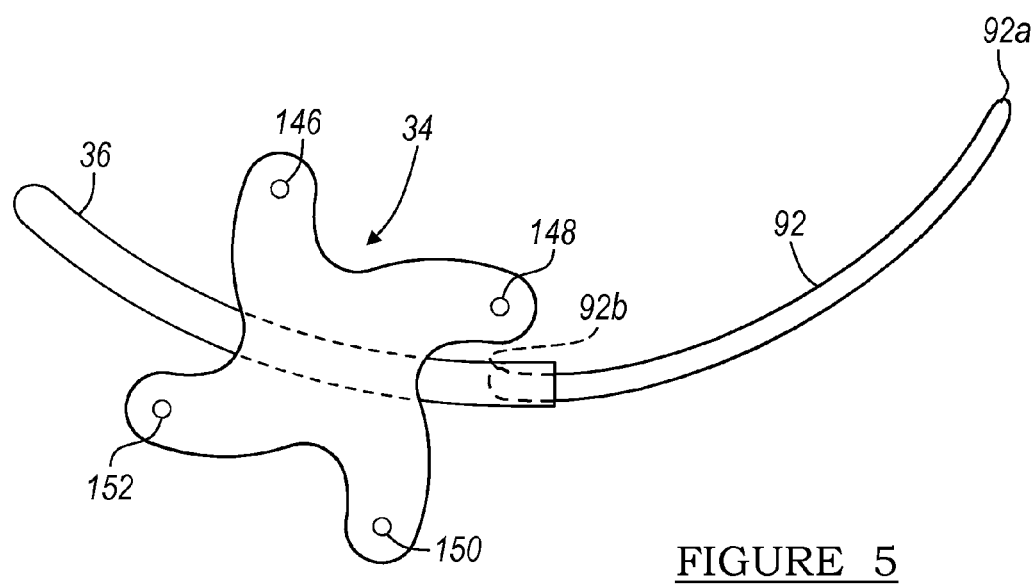
FIG. 5 is a navigable instrument to assist in positioning a connector according to various embodiments.

With reference to FIG. 5, the instrument 36 may be any appropriate instrument, such as an instrument that is operable to engage one of the connectors 88, such as the connector 92. The instrument 36 also includes the tracking element 34, which includes a plurality of tracking points, such as tracking points 146, 148, 150, and 152. The tracking element 34 is detectable by the detector 22 so that the navigation computer 24 is able to determine the location of the instrument 36 and hence the location of the connector 92.

The instrument 36 engages the connector rod 92, such that the instrument 36 is able to move the distal end 92a of the connector 92 in a selected manner. A proximal end 92b of the connector 92 is removably engaged to a portion of the instrument 36. The connection between the rod 92 and the instrument 36 may be any appropriate connection. Nevertheless, the instrument 36 may be used to move the rod 92 during the procedure.

The location of the distal end 92a may be determined by the location of the instrument 36 because the rod 92 is generally rigid. Therefore, the position of the rod 92, and particularly, the position of the distal tip 92a may be determined relative to the tracking element 34, such that movement of the distal tip 92a can be determined by a movement or location of the tracking element 34.

Nevertheless, as discussed above, the connector 88 need not necessarily be a rigid connector. When the connector 88 is substantially not a rigid connector, a different tracking element may be positioned relative to the connector 88. For example, the connector 88 may include an EM coil or multiple coils that are able to be tracked by the tracking apparatus 20 if the tracking apparatus includes an EM tracking system. Therefore, the connector 88 may be tracked using the EM sensor coils to determine the position of the connector 88. Alternatively, the connector 88 may be generally steerable such that a user may steer the connector 88 along a selected path. In this instance, the computer may be able to inputted with the distance the connector 88 has traveled, the number of turns, the severity of the turns, the distance traveled along a selected turn, such that a distal end point of the connector 88 may be determined knowing each of these known distances and turns. Again, it will be understood that these are merely exemplary of different ways of tracking the connector element 88 during a procedure. Therefore, it will be understood that the present disclosure and the appended claims are not so limited by such examples.

Various instruments and apparatii have been above disclosed. Generally, the localization system or navigation system 20 is able to localize the construct portions 80 implanted in an anatomy and also able to determine the location and assist in navigation of the connector 88 during an imageless procedure. Although the instrument 36, the construct portions 80, and the localization and navigation apparatii 20 may differ, a method of using the various elements will now be described.

Figure 6:
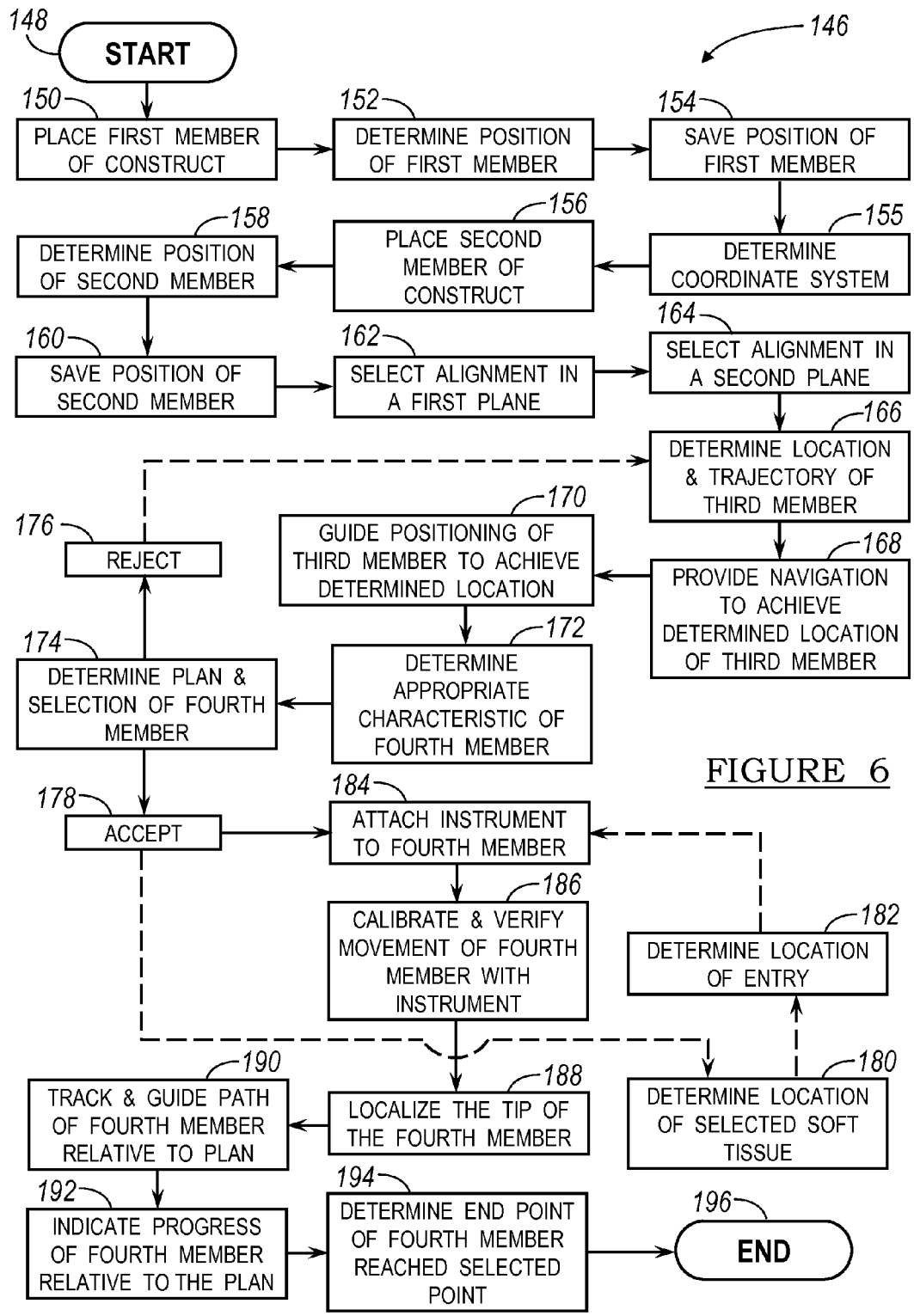
FIG. 6 is a flow chart for a method of implanting and navigating a selected construct according to various embodiments.

With reference to FIG. 6, a general method for performing a imageless procedure to implant a construct is illustrated in the flow chart 146. The method or program 146 generally begins at a start block 148. At the beginning of the procedure, a first member of the construct is implanted in block 150. As discussed below, the first member may include a first pedicle screw that may or may not be cannulated. Next, the position of the first member is determined in block 152. As discussed above, and further herein, the localization element 104 may be used to determine the first position. Nevertheless, and as discussed further herein, various other techniques may be used to determine the position of the first member. For example, the instrument 36 may also be a probe that may simply contact the screw to identify the corresponding location. After the position of the first member is determined, the position may be saved in block 154. Generally, the position of the first member is saved in block 154 and can be used as the reference for determining relative locations of other members, after the implant. Again, the position may include x, y, z positions and/or orientations.

After the position of the first member is saved in block 154, an optional determination of a coordinate system may be determined in block 155. Although the determination of the coordinate system may occur after saving the position of the first member in block 154, the determination of the coordinate system may occur at any time. For example, a coordinate system relative to the user 30, the patient 40 or any appropriate coordinate system may be determined. This determination may occur before positioning the first member or after positioning any appropriate number of members. Generally the coordinate system assists the user 30 in determining an orientation of the members relative to the patient 40. Also, the coordinate system may assist in orienting an atlas or 3-D model on the display 28 relative to the members of the construct, as illustrated herein. The coordinate system, therefore, may include any appropriate number of coordinates, such as X, Y or X, Y, Z.

Generally, the coordinate system may be determined by sensing a location of a position of the patient 40 relative to the first implant. As described herein, this may be done by determining a position of the first member in block 152 or may be done as a separate step. For example, the user may touch a relative superior portion of the patient 40 and input the position into the navigation computer 24 followed by touching a relative inferior, lateral, medial, or any appropriate position. Alternatively, the coordinate system may be determined by contacting several portions of the anatomy of interest (i.e., vertebra) and using surface recognition software to identify the orientation of the region of interest. The coordinate system may be determined in block 155 in any appropriate manner. In addition, as discussed herein, the coordinate system may also be fine tuned or determined when determining a location of the selected soft tissue in block 180. Nevertheless, it will be understood that determining coordinate system is not necessary to the method 146 and is merely optional.

As discussed above, the field reference or dynamic reference frame 38 may be positioned to determine the relative location of all elements relative to the dynamic reference frame 38. The dynamic reference frame 38 may be used for procedures where the patient may move during the procedure. in such a situation use of the dynamic reference frame 38 may increase accuracy. For lower spinal fusion, however, movement of the patient is at best minimal and the dynamic reference frame 38 is generally not required. Nevertheless, in addition to and alternative to the field localizer 38, the position of the first member may be saved as a "true" location or reference. This may be especially the case when the position into which the first member is fixed is substantially immobile. Therefore, all other points that are formed relative to the position of the first member can be known relative to the position of the first member and various determinations may be based thereupon. In addition the construct may be assembled only knowing the relative location of the implanted members. In this case the navigation computer may determine the location of each element in real time.

With continuing reference to FIG. 6 and the method of 146, placing a second member of the construct is performed in block 156. As discussed above, the second member may include a second pedicle screw positioned in a vertebra. After the second member is positioned, determining the position of the second member is performed in block 158. Also as discussed above, determining the position of the second member may include positioning the second localization element 106 relative to the second member. Nevertheless, also as discussed above, various other techniques may be used for determining the position of the second member or the first member as discussed in block 152. Nevertheless, the position of the second member may be determined through any appropriate method. For example a navigable needle may be used to touch or indicate a location of the second member. The position of the second member relative to the first member is saved in block 160.

The position of the second member may also be a "true" position. That is, both the position of the first member and the position of the second member may be generally determined and known by the computer 24. In this case a localization element would be attached to each member during the procedure and would be essentially act as a dynamic reference frame for each member. Generally, the positions of the first member and the second member saved in blocks 154 and 160 respectively, are saved in the navigation computer 24 for display on the monitor 28. In addition, the navigation computer 24 is able to use these locations for various other portions of the procedure.

After the position of the first member and the second member are saved, the computer 24 may assist or be used to determine placement of various other elements of the construct. An alignment of the anatomy, relative to the construct and to be formed by the construct, can be selected in the first plane in block 162. Similarly, an alignment in the second plane may be selected in block 164, again for use with or to be formed by the construct. The alignment in both the first and the second planes are selected in blocks 162 and 164, respectively, may also be suggested by the computer 24. These planes are generally positioned orthogonal to one another, but may be positioned at any appropriate angle relative to one another.

The computer 24 may suggest an alignment to be produced in the anatomy based upon generally known portions of the construct, as described herein. For example, as described above, the construct may include a plurality of connectors 88 each including a different characteristic. Therefore, the computer 24 may assist in suggesting a position of a third member to assist in forming an alignment that would allow for implantation of a selected or known connector. In addition, it will be understood, that any number of planes or alignments may be suggested or selected. Simply the inclusion of two planes for selection is for clarity of the following discussion, but will be understood that any appropriate alignment, even outside of a selected plane, may be determined and selected.

After the selected alignments are chosen in blocks 162 and 164, a location of a third member may be determined in block 166. Generally, the location of the third member determined in block 166 may allow for achieving the selected alignments in the first plane and second planes selected in blocks 162 and 164. Again a user or the computer 24 may select the location of the third member to achieve the selected alignment.

Real time navigation may be provided for positioning the third member in the determined location in block 168. Although various techniques may be used for providing the real time navigation, a navigated needle or probe 236 or 246 (FIGS. 9B and 11A) may be used to ensure that a selected trajectory, to achieve the determined location of the third member in block 166 is assured. In addition, the navigated needle may act as a guiding member such that the screw may be guided into the anatomy using the navigated needle to achieve the determined location in block 166.

During the positioning of the third member, the third member can be guided to align the third member according to a characteristic of a fourth member. For example, as discussed herein, if the third member is a screw, the third screw may be positioned distally and proximally to ensure that the fourth member, that may include the connector 88, may be positioned relative to each of the three members in a selected orientation.

An indication of the length and other characteristics, such as the radius, of a fourth member may be indicated in block 172. The indication may occur at any appropriate time, such as once the third member has been positioned and guided to ensure that the appropriate orientation and location is achieved, That is, the position of each of the three members is known such that a length between the three members and a radius achievable with the positioned members, or other characteristics defined by the three members, may be known and displayed on the monitor 28.

The user may select a fourth member based upon the shown characteristic. The determination of the fourth member is generally achieved by positioning the third member in a selected location. Nevertheless, it will be understood that any appropriate number of members may be provided. The positioning of generally three members and the interconnection of the three members with the fourth member is simply exemplary. For example, only two members may be positioned and a third member interconnect those two members. Alternatively, any number of members may be fixed in a selected portion of the anatomy and a connector used to interconnect each of the plurality of members. Therefore, only providing three members and interconnecting them with the fourth member is not intended to limit the disclosure or the scope of the appended claims.

After the appropriate fourth member characteristic or fourth member has been chosen, the user may accept the plan including the choice of the fourth member. The user may Decline in block 176 the plan as outlined in block 174. In this case, the position of the third member can be further guided in block 170. The guiding and the positioning of the third member may require movement of the third member such that a different location may be achieved. This different location may then be used to determine a new appropriate characteristic for the fourth member in block 172 in providing a new plan outlined in block 174. Once the user agrees with the plan as determined in block 174, the user may Accept in block 178 the plan outlined in block 174. After the plan is accepted, other points for navigation may be determined to assist in the navigation of the procedure or the procedure may proceed only using those points already determined and the information generally available to the user.

After accepting the plan various other characteristics, relative to the anatomy, for implantation may be determined. For example, a location of the soft tissue surrounding the implantation site may be determined in block 180 and a location of entry may be determined in block 182. Although it will be understood that the determination of a location or contour of the soft tissue in block 180 and the location of an entry point termination in block 182 is not necessary, such determinations may be useful in the implantation procedure.

Determining a location of the soft tissue relative to the implantation area may include dragging an instrument over a surface or determining a plurality of points of a surface of the soft tissue surrounding the implant area, such as the spine, relative to the first, second, and third members, using a selected probe. In an example, the probe 246 (FIG. 11A) may be interconnected with the navigation computer 24 or may be detected with a detector 22 such that a contour of the soft tissue relative to the implantation area of the first, second, and third members may be determined. The contour determination may be performed by providing a probe that may be touched to the skins surface in a plurality of points to determine a contour of the soft tissue. Once the contour of the soft tissue is determined, a specific location for entry of the fourth member may be determined and selected in block 182.

The contour of the soft tissue may be determined such that the navigation computer 24 may assist in selecting an entry point for the fourth member to assist in implanting the fourth member relative to the first, second, and third members, or any appropriate number of members. As described herein, this may assist the user in insuring a substantially easy implantation in alignment of the first, second, and third members during the implantation of the fourth member.

Also, the location of other appropriate soft tissues, such as tendons or ligaments, may be known and used to assist in providing information to the navigation computer to balance the sheer forces of the construct relative to the soft tissue after the implantation of the construct. Therefore, the navigation computer 24, or a user, may determine or input a location of the soft tissue, position of the soft tissue, or position of a soft tissue implant, to provide a selected tension, stress, or other forces, on the construct. For example, it may be desirable to balance the forces among each of the portions of the construct, and positioning soft tissue or knowing the position of the soft tissue may assist in such balancing.

Because of the determination of the location of the selected soft tissue in block 180 and the determination of a location of entry in block 182 is not necessary these blocks may simply be skipped and after accepting the plan in block 178, the fourth member may be attached to a selected instrument in block 184. Alternatively, the selected member may be attached to the instrument after or relative to determining location of the soft tissue in block 180 and determining a location of entry in block 182. Nevertheless, the fourth member, which may include the connector 88, is generally affixed to the instrument, as illustrated in FIG. 5.

The instrument 36 may be any appropriate instrument and is generally illustrated to be a clamp member that may selectively engage the connector 92 for the procedure. Calibration and verification may occur of the fourth member relative to the instrument in block 186. This allows the navigation computer 24 to be able to verify or determine a position of the connector, such as the distal end 92*a*, relative to movement of the instrument 36. Once the calibration and determination is completed, the navigation computer 24 may use the information provided by the detector 22 to determine position of the end distal portion 92*a* or the connector 92 due to movements of the instrument 36 in the interconnected location elements 230.

Once the calibration and verification of the fourth member relative to the instrument is performed in block 186 the tip, such as the distal end 92*a* of the connector 92, can be localized in block 188. Generally, the position of the tip may be localized relative to a selected path of the fourth member. This may be done in any appropriate manner, such as that described herein, but generally may be schematically indicated as a crosshair on the monitor 28 relative to a selected path which may be illustrated as a circle.

Once the tip of the fourth member has been localized in block 188 movement of the fourth member may be tracked and guided in block 190 relative to the plan determined in block 174 and accepted in block 178. Generally, although various techniques and illustrations may be used, the movement of the fourth member may be tracked due to the fixation of the fourth member relative to the instrument 36 which includes the localization element 230 such that the movement of the instrument 36 may be used to determine a position of the fourth member. The movement of the fourth member may therefore be illustrated as the movement of a crosshair on the monitor 28 and illustrated relative to a circle which may dynamically indicate the planned position of the tip of the fourth member relative to the actual position of the tip of the fourth member.

As the fourth member is moved relative to the first, second, and third members, such as during the implantation procedure, a real-time indication of the progress of the fourth member relative to the plan may be illustrated in block 192. In this way, a user may determine the progress of the fourth member to understand the position of the fourth member relative to the first, second, and the third members and other portions of the anatomy. In addition, the indication of the progress may illustrate the position of the member relative to the anatomy to allow for any adjustment that may be necessary due to selected anatomical portions, peculiarities of the anatomy, the particular area into which the fourth member is being moved, or other various considerations. In addition, the progress of the fourth member may be used to determine an end point to the fourth member has reached a selected point in block 194.

Generally, the tip of the fourth member, including the distal end 92*a*, may selectively reach the second member, which may be an end point of the implantation procedure. Nevertheless, the determination of the fourth member reaching the selected point may indicate that the procedure has achieved a selected result and the procedure may generally end in block 196. Although it will be understood that a surgical procedure may not simply be completed with the implantation of a fourth member, and it may include various other procedures such as stitches to close any incisions, the application of various medications and antibiotics, or other appropriate applications, the navigation of the fourth element to the selected end point may generally end the navigation procedure.

It will also be understood that the method 146 need not simply be limited to the navigation of the construct 80 relative to a selected anatomy. For example, a construct such as a multi-element acetabular implant, femoral implant, humeral implants, tibial implant, bone plate, combinations thereof, or any appropriate implant may be guided using the method 146. Generally, any selected first member may be implanted and a second member may be imagelessly guided relative to the other members to achieve a selected result.

In addition, it will be understood that the method 146 need not necessarily be limited to use for implantation relative to an anatomy. For example, the method 146 may be used to position a member in any visually restrictive location, such as building a wing element of an airplane, an internal engine, or any position which may limit the optical visualization by a user of the location of a selected member. In addition, the method 146 may be used to position a first member relative to a second member from locations that are known due to pre-saved or detected location such that members may be moved relative to one another.

As an exemplary use of the method 146 for implanting a construct, such as a spinal implant, is included in the following description but is intended only to be an exemplary use of the method 146. Therefore, it will be understood that the method 146 may be used to implant any appropriate implant, but may also be used to implant the construct 80.

Also, as discussed herein, the procedure is performed substantially without capturing patient images, regardless of when acquired, with any imaging device, such as the optional imaging device 50. The navigation system 20 may navigate the various portions, including the instrument 36, relative to known points, such as the position of the first screw 206 or the dynamic reference frame 38. Generally, the positions of these would be shown as icons alone on the display 28. Nevertheless, an unmorphed atlas map of the spine, or any other appropriate portion, may also be superimposed over the icons or vice versa of the implanted portions for any appropriate reason. Regardless of the icons on the display 28, registration of images is not required for appropriate performance of the procedure. As discussed herein, patient images may be acquired for confirmation of the proper placement of the construct, or any other appropriate reason, but images of the patient, such as those that may be acquired with the optional imaging system 50, are not required.

Figure 7A:
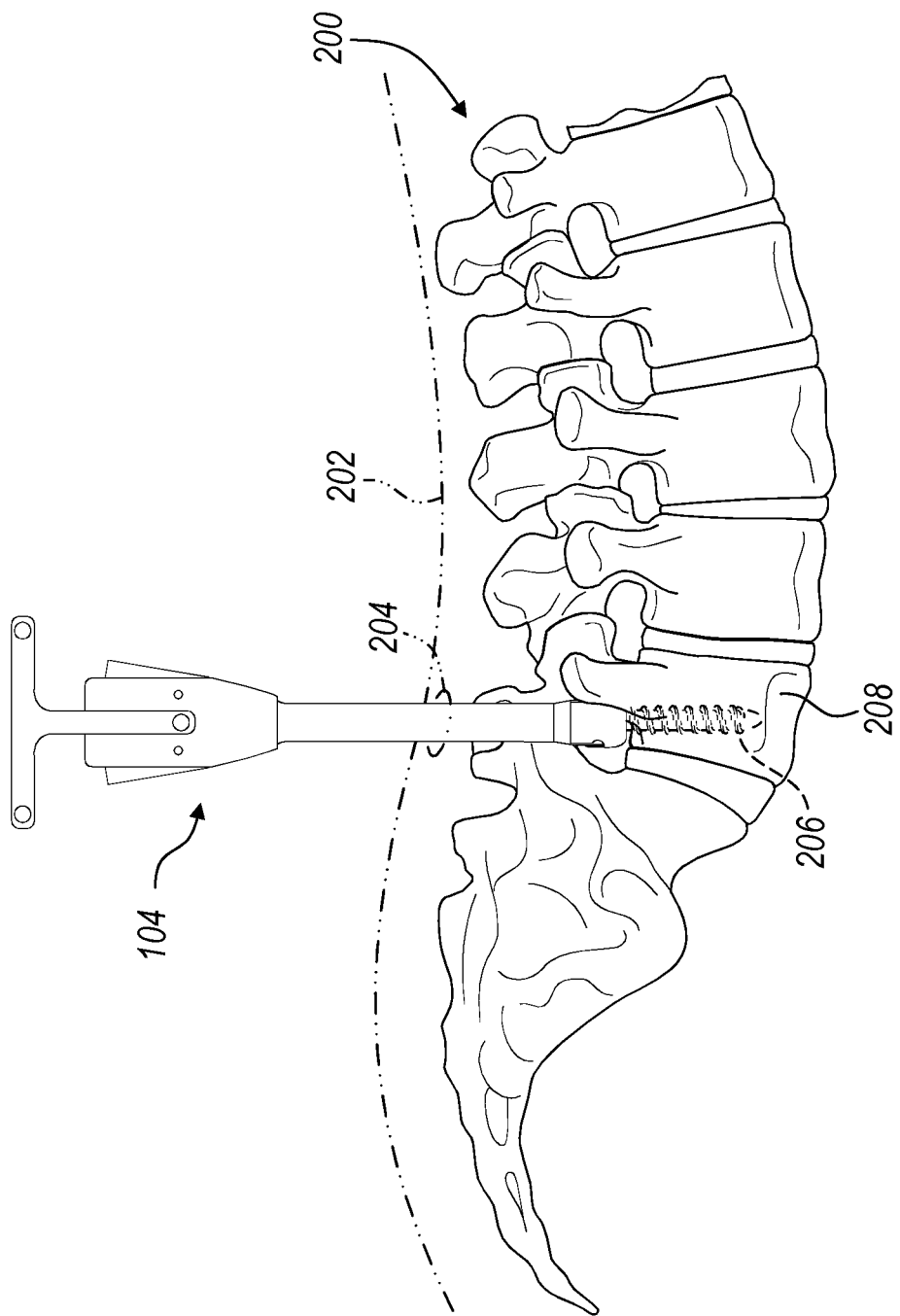
FIG. 7A is a partial detailed view of a portion of a spine including a portion of a construct localization element affixed thereto.

With reference to FIG. 7A, an exemplary construct 80 may be implanted relative to a selected portion of a spine 200 using the method of FIG. 6. The spine 200 is generally surrounded by soft tissue, such as a dermis 202 and other muscles and tendons, not particularly illustrated. Nevertheless, it will be understood that an incision 204 is generally formed through the soft tissue, including the dermis 202 to obtain percutaneous and/or minimally invasive access to the spine 200. That is the procedure is generally not open and includes little or no direct viewing of the spine. This allows the procedure to be minimally invasive and/or percutaneous to reduce stress to the patient and healing time. The following description may reference the method 146 illustrated in FIG. 6 generally and specifically to the processes occurring for the exemplary implant of the construct 80.

It will be understood that the following method may be used in conjunction with a patient image of the spine, such as one acquired with the optional imaging system 50, to be performed with images. Nevertheless, it will be understood that the process and the method is generally performed without use of any anatomical patient images such that the method may be performed substantially imageless or simply include an atlas model. As exemplary illustrated herein, the monitor 28 may display a patient image, that may be preacquired or acquired intraoperatively. Similarly, an atlas model may be displayed on the monitor 28 that may be morphed relative to known sizes and orientations of the spine 200 on which the procedure is performed. Typically, however, no preacquired images are obtained and the monitor 28 may simply display icons representing the positions of the various members, including the screws 82, and other selected points, thereby eliminating the need for registration and of capturing patient images.

With reference to FIG. 6 and FIG. 7A, the process is generally started in block 148. As discussed above, the incision 204 and optional preacquired images may be obtained prior to or at the start block 148. After the incision 204 is formed, a first screw 206, is positioned in a predetermined position, such as a first vertebrae 208. It will be understood that the first screw 206 may be positioned in any appropriate location.

Nevertheless, once the first screw 206 is positioned in the first vertebrae 208 the position of the first screw 206 can be determined, such as determining the position of the first member in block 152. The position of the first screw 206 can be determined by positioning the first localization element 104 relative to the first screw 206. As discussed above, the localization member 104 may include the extender 116 that is able to selectively engage a portion of the first screw 206. In addition, the localization unit 104 includes the tracking element 110 that includes portions that may be detected by the detector 22, such as detectable portions 120, 122 and 124. Therefore, after the first screw 206 is inserted into the vertebrae 208, the localization unit 104 may be affixed thereto. The localization unit 104 is used to determine the location of the first screw 206. The detector 22 detects the location of the tracking element 110, such that the detected location can be transmitted to the navigation computer 24 and illustrated on the monitor 28, via an icon representing the first screw 206.

The localization element 104 may be able to provide any selected information. For example, the localization element 104 may be keyed to a selected shape of the first screw 206, such that the localization element 104 may engage the first screw 206 in substantially only one manner. In this way, the trajectory, rotational position, and location of the first screw 206 may be determined with six degrees of freedom information. In addition the axis of the screw head 86 may be determined if the screw 206 is a multi-axis screw. Although this is not required, it may be selected to determine this information depending upon the implant being implanted, such as the construct 80 where the connector 88 is selected to engage the screws in a selected manner.

In addition, the localization element 104 may include any appropriate localization portion different from the tracking element 110. For example, an optical based tracking element may be included as a tracking element 110 or selected coils may be positioned relative to the tracking element 110, such that an EM system may be used to determine the location of the first screw 206. Also, the first screw 206 may include internally contained elements, such as coils, that are able to be located using an EM location system. Therefore, it will be understood that the localization elements, 104, 106, and 108 are only exemplary apparatuses to determine the location of the first screw 206. Moreover, by having localization element 104 continuously affixed to screw 206, no dynamic reference frame 38 is required since any movement of the vertebrae will be detected by the detector 22, via localization element 104. Alternatively, a navigatable needle or probe 246 (FIG. 11A) may simply be used to contact the screw 200 to determine its location. In which case, a dynamic reference frame 38 attached to the vertebra of interest may be helpful.

Figure 7B:
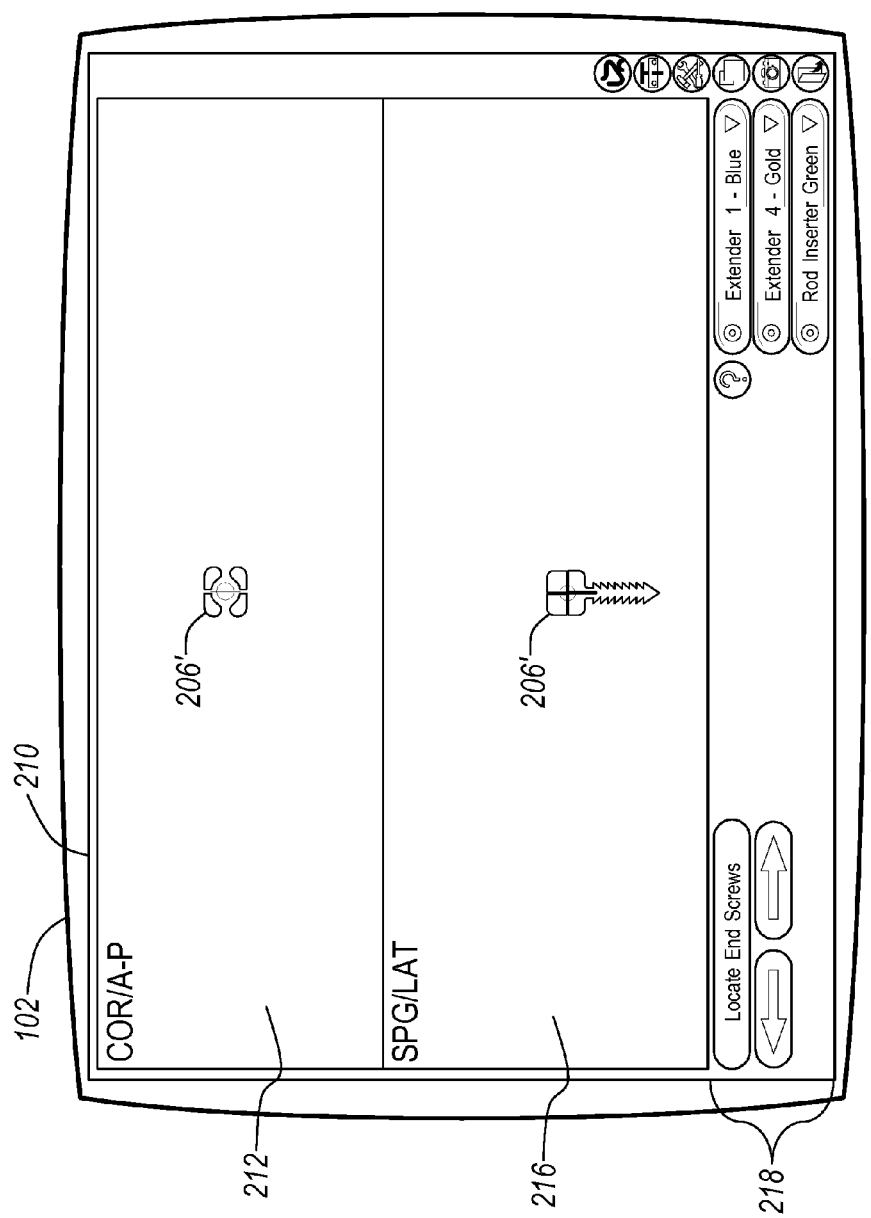
FIG. 7B is a screen produced by the navigation system display indicating a location of a first portion of a construct.

After the location of the first screw is determined, such as in block 152 the location of the first screw 206 is saved in the navigation computer 24, such as included in block 154 where the position to the first member is saved. Therefore, the position of the first screw may be illustrated on the monitor 28. With reference to FIG. 7B, the monitor 28 may be any appropriate monitor, such as a cathode ray tube, liquid crystal display, plasma display, or a goggle display for individual viewing. Nevertheless, the monitor 28 may display a selected screen 210 that may include any appropriate portion.

For example, the screen 210 may include a top section 212 that illustrates an anterior/posterior plane view or a representation of the first screw 206. The representation of the first screw 206, is a substantially virtual first screw 206' on the screen 210. The location of the first screw 206 can be illustrated as the virtual first or first icon screw 206' due to the detection by the detector 22 of the localization element 104. Although other appropriate mechanisms may be used to localize the first screw 206. The screen 210 may also include a bottom portion or second portion 216 that illustrates a substantially lateral plane view of the first screw 206 as a cross-section or profile of the first virtual screw 206'. It will be understood that any appropriate views may be represented on the screen 210 and only including the anterior posterior plane view in section 212 and the lateral plane view in section 216 is simply exemplary and not intended to limit the present disclosure. Nevertheless, the virtual screw 206' may illustrate the rotational position, the trajectory, the location, and any other attributes collected due to the saving of the first position of the first screw 206.

In addition, the monitor 28 may be a touch sensitive monitor, such that touch button 210 may be included on the monitor 28. The touch buttons may allow for the selection of which localization element is connected to the screw and may be used for later navigation purposes. It will be understood, however, that the touch buttons 218 are merely exemplary and not required. For example, the touch buttons 218 may also be selectable by a pointer device, such as a generally known mouse, or commands and selections may be substantially manually entered with a keyboard or the like.

Figure 8A:
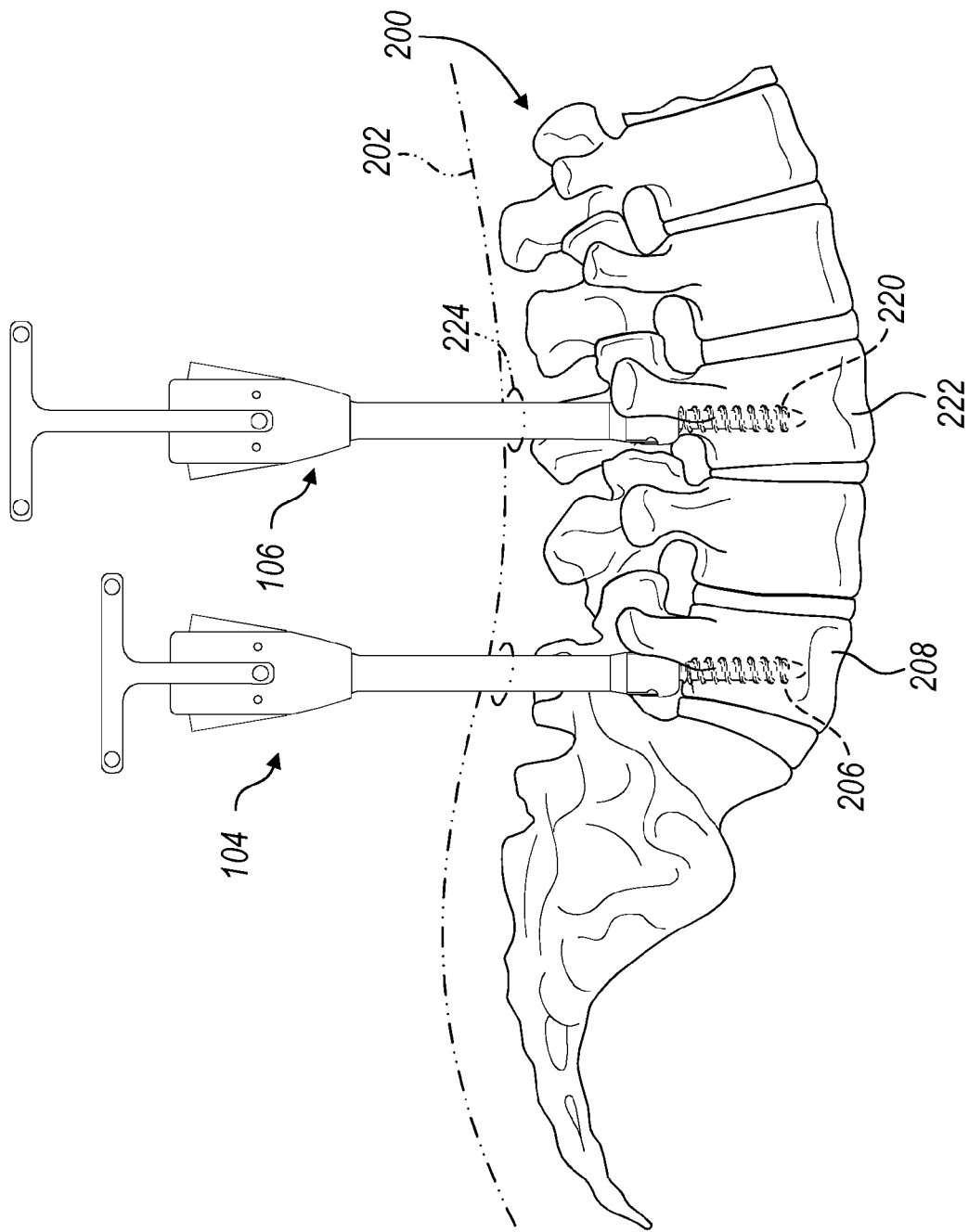
FIG. 8A is a partial detailed view of the spine including two portions of a construct and a localization element affixed thereto.

With reference to FIG. 8A and continuing reference to FIG. 6, a second screw 220 may be positioned in a second vertebrae 222. Positioning the second screw 220 is exemplary of placing a second member in block 156. The second screw 220 is also generally positioned through the dermis 202 through an incision 224 formed therein. It will be understood that the second screw 220 is generally positioned through similar soft tissue as the first screw 206. Therefore, the screw 220 can be positioned into the second vertebrae 222 through any generally known method.

The position of the second screw 220 may then be determined, such as determining the position of a second member in block 158 of the method 146, using a second of the localization element 106. The second localization element may include the extender 126, which is able to operably engage the second screw 220. As discussed above, the extender 126 may engage the second screw 220 in any appropriate manner, which may include a substantially quick release manner using the levers 134. The second localization element 106 generally includes the tracking element 112, which includes the navigation areas 128, 130 and 132, such that the detector 22 may detect the position of the tracking element 112. The dimensions of the extender 126 relative to the second screw 220 and a tracking element 112 are generally known and can be selected using the computer 24. Also, as discussed above, the position of the second screw 220 may be determined using any appropriate mechanism.

Therefore, the detector 22 may detect the position of the tracking element 112 and transmit the information to the computer 24, such that the location of the second screw 220 may be determined both independently and/or relative to the first screw 206. The position of the second screw 220 may be saved, such as saving the position of the second member in block 160 of the method 146. As with the position of the first screw 206, the position of the second screw may be illustrated on the screen 210. Alternatively, the navigated needle or probe 236 (FIG. 9B) may be used to sense the location of the second screw. After sensing the location of the second screw 220, its location may be known relative to the first screw 206. When the localization element 108 is not attached to the second screw 220, the dynamic reference frame 38 may be referenced to determine the position of the second screw 220 if there is any movement of the vertebrae. It will be understood any number of implant portions may be sensed. In addition, a plurality of constructs may be sensed and interconnected. Therefore, providing only one construct or one connector is merely exemplary and not limiting.

Figure 8B:
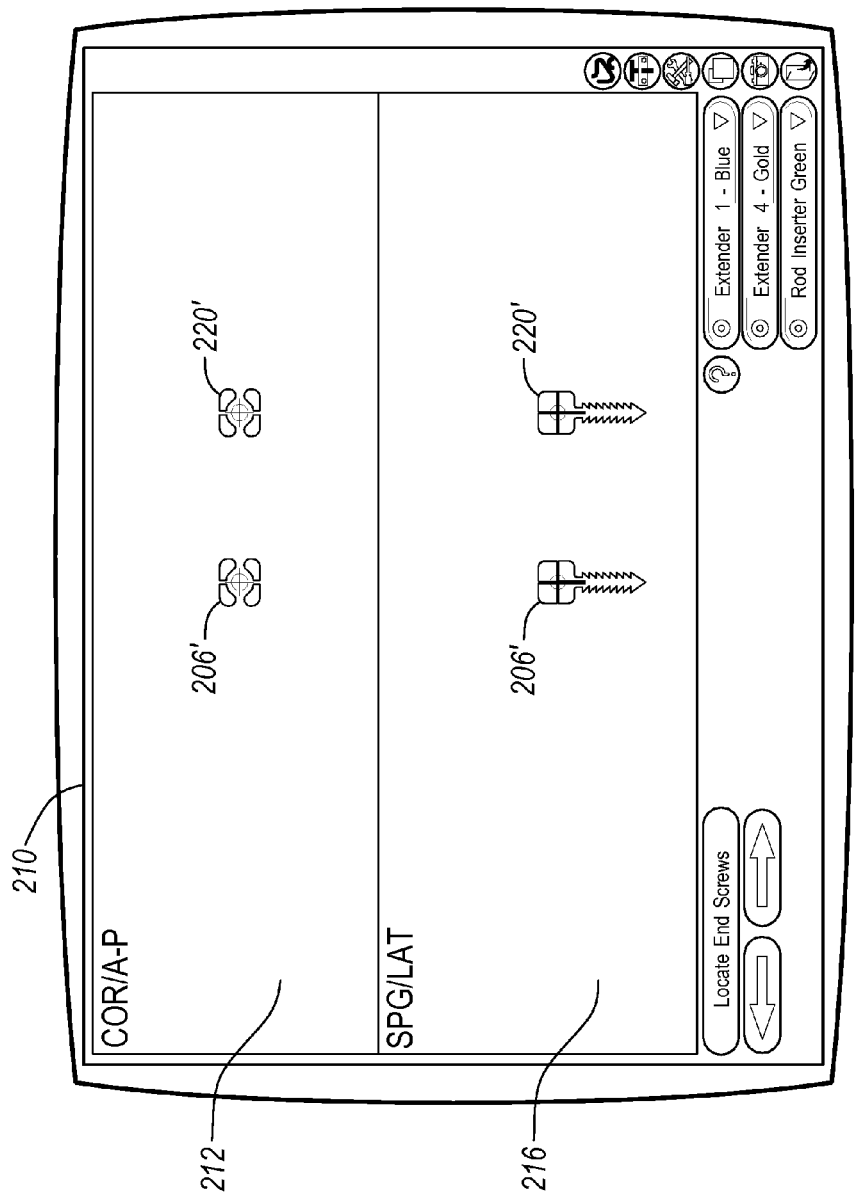
FIG. 8B is a screen produced by a surgical navigation system including two portions of the construct.

With reference to FIG. 8B, after the detector 22 has detected the position of the second screw 220, a second virtual screw 220' is illustrated on the monitor 28. The screen 210 may change to illustrate the second virtual screw 220'. Substantially similar views of the second virtual screw 220' may be illustrated similar to those of the first virtual screw 206'. For example, an AP plane view of the second virtual screw 220' may be illustrated relative to the first virtual screw 206', such that the relative locations and measurements may be obtained relative to the first virtual screw 206'. Similarly, a lateral plane view may illustrate a substantially cross section or profile view of the second virtual screw 220' similar to the virtual first screw 206'. Nevertheless, the monitor 28 is able to illustrate on the screen 210 the relative position of the first screw 206 as the first virtual screw 206' and the second screw 220 as the second virtual screw 220'.

Once the location of the first screw 206 and the second screw 220 have been saved on the navigation computer 24 the relative distances, orientations, and the like may be illustrated on the screen 210. Therefore, a user is able to determine the position, location, displacement, and other attributes of the first screw 206 relative to the second screw 220, although the first screw 206 is not viewable and neither is the second screw 220 through the dermis 202. The virtual display of the first virtual screw 206' is displayed relative to the display of the second virtual screw 220' so that this information may be known.

Figure 9A:
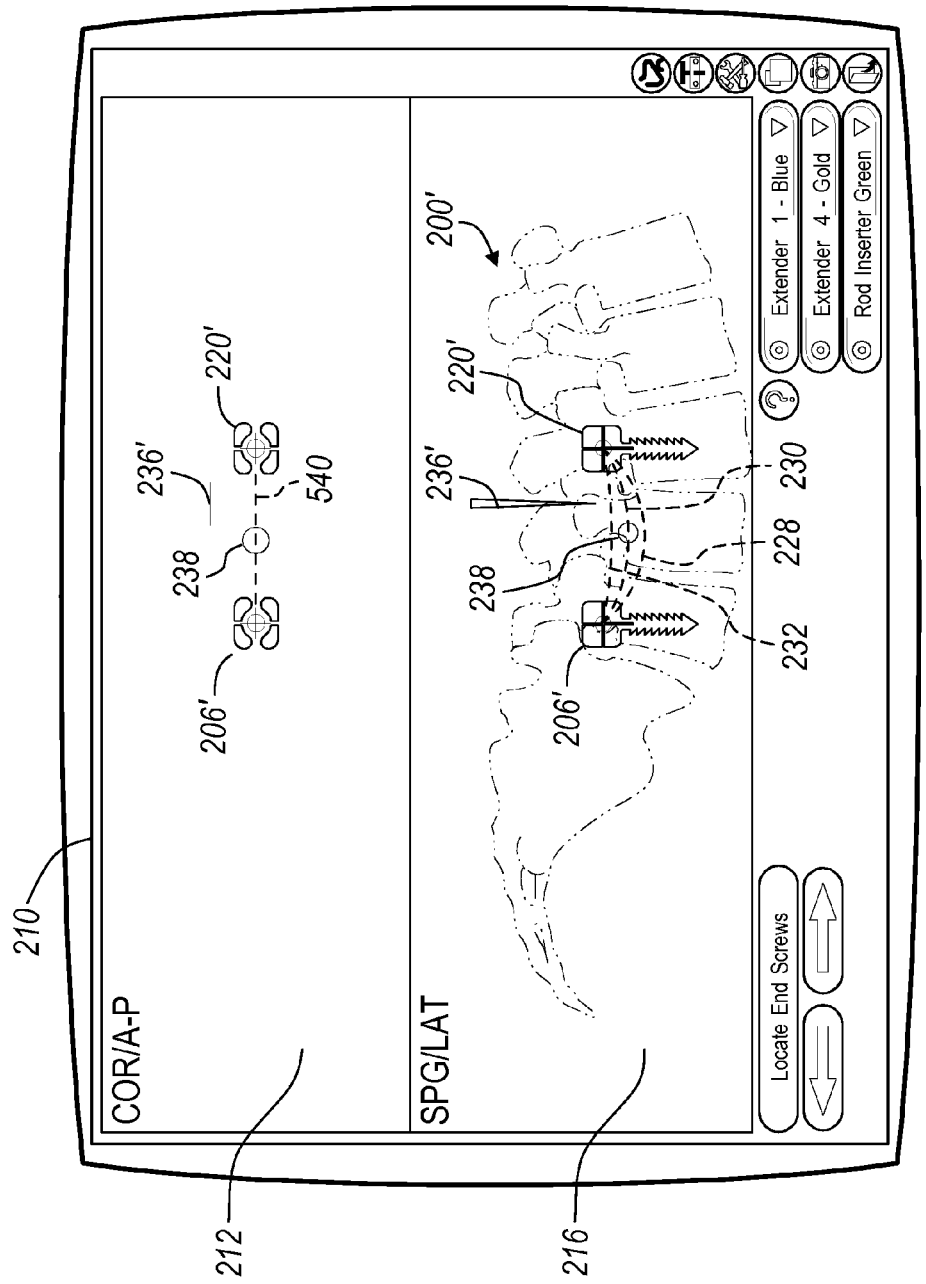
FIG. 9A is a display produced by the surgical navigation system for planning the procedure.

With reference to FIG. 9A, the information displayed on the screen 210 illustrates a substantially virtual view of the anatomical occurrences. Therefore, the anatomical portion may not change, but the screen 210 and the computer 24 operably connected thereto may be used to plan further portions of the procedure.

The first virtual screw 206' and the second virtual screw 220' may be shown alone on the screen 210 or may be shown in conjunction with an image of the spine 200. The image of the spine may be an image acquired pre- or intra-operatively of the patient 40. For example, if the fluoroscopic device 52 is included in the procedure, a real-time image of the spine 200 may be taken and illustrated relative to the first virtual screw 206' and the second virtual screw 220' on the screen 210. The first screw 206 and second screw 220 may also be generally radial opaque. Therefore, the image taken of the spine 200, including the first screw 206 and the second screw 220, may be used to verify the representation of the first virtual screw 206' to the second virtual screw 220'. In addition, the image of the spine may be superimposed over the first virtual screw 206' to the second virtual screw 220' to give a visual cue of the anatomical portions specifically near the screws 206 and 220. Although the inclusion of the image of the spine is not necessary, it may be selected to include the image of the spine.

The image of the spine may also be achieved by using a generally known atlas that is morphed to the patient 40 using pre-acquired or intra-operatively acquired images. The morphed atlas image may be morphed relative to the specific anatomy of the patient 40. In addition, the position of the screws in the anatomy may be known and the morphed atlas image of the spine be morphed or augmented, such that the known locations of the first screw 206 and second screw 220 substantially meet the size indications of the morphed atlas image. Therefore, the spine image may either be an image of the patient 40 or a morphed atlas image that may be stored in the navigation computer or accessed by the navigation computer 24.

Nevertheless, and as may be typically performed, a virtual or representative spine 200' may be displayed as an icon or representation of the spine 200. The virtual spine 200' may be a generally known atlas model or computer generated representation of the vertebrae relative to the screws 206 and 220. Therefore, the display may include the icons of the screws 206' and 220' also, or in addition, to an icon or graphical representation of the spine 200. The virtual spine 200' is not necessarily directly representative of the spine 200 and may simply be for user comfort while the positions of the screws 206 and 220 are known and represented as the first virtual screw 206' and the second virtual screw 220'.

If a virtual image, such as from an atlas model or a 3D model, is used to form the virtual spine 200' on the screen 210, the atlas or 3D model may be morphed relative to any known measurement. For example, the 3D model or atlas model may be morphed relative to the size of the screws implanted into the spine 200. Therefore, the atlas or 3D model may be morphed or scaled to the size of the implanted screw due to the inputted information about the screw into the navigation computer 24. Information regarding the size of the screw relative to a size of the vertebrae or the pedicle into which the screw is placed may be used for the scaling. Therefore, a generally known atlas or 3D model may be morphed knowing the size of the screws implanted or any other known measurement, such as also a pre- or intra-operatively acquired image, if one is acquired.

Regardless of whether the screen 210 includes the virtual spine 200' or an image of the spine 200, the determination of various aspects of the procedure may occur. For example, an alignment in the AP plane may be selected or suggested, such as selecting an alignment in the first plane in block 162. An alignment display line 226 may be displayed in the AP section 212 of the screen 210. The anterior posterior alignment line 226 may either be selected by a user or suggested by the navigation computer 24 depending upon selected inputs. The anterior posterior alignment line 226 may be used for any purpose, such as ensuring a substantially straight line between the first screw 206 and the second screw 220, such as represented by the first virtual screw 206' and the second virtual screw 220'. Nevertheless, it will be understood that the alignment line 226 may be used to choose any appropriate or selected alignment of the anatomy relative to the virtual screws 206' and 220' or to any portion outside of the virtual screws 206' and 220'. That is, the alignment line 226 may be used to align a position generally between the first virtual screw 206', therefore, the first screw 206 and the second screw 220', and therefore, the second screw 220, or to any point outside of the two screws 206 and 220.

In addition, an alignment in a second plane, such as the lateral plane, illustrated in the second section 216 may be selected or chosen, such as selecting alignment in a second plane in block 164. Any appropriate alignment, such as a selected radii may be illustrated or chosen in the second section 216. For example, three possible radii 228, 230, and 232 may be illustrated between the first virtual screw 206' and the second virtual screw 220'. The radii may be suggested by the navigation computer 24 or selected by the user. Nevertheless, a plurality of the radii lines may be illustrated in the second section 216 of the screw 210 for selection and use by the user. The display of the various alignments or radii in the second section 216 allows the user to determine or select the radii most appropriate for the procedure.

Figure 10A:
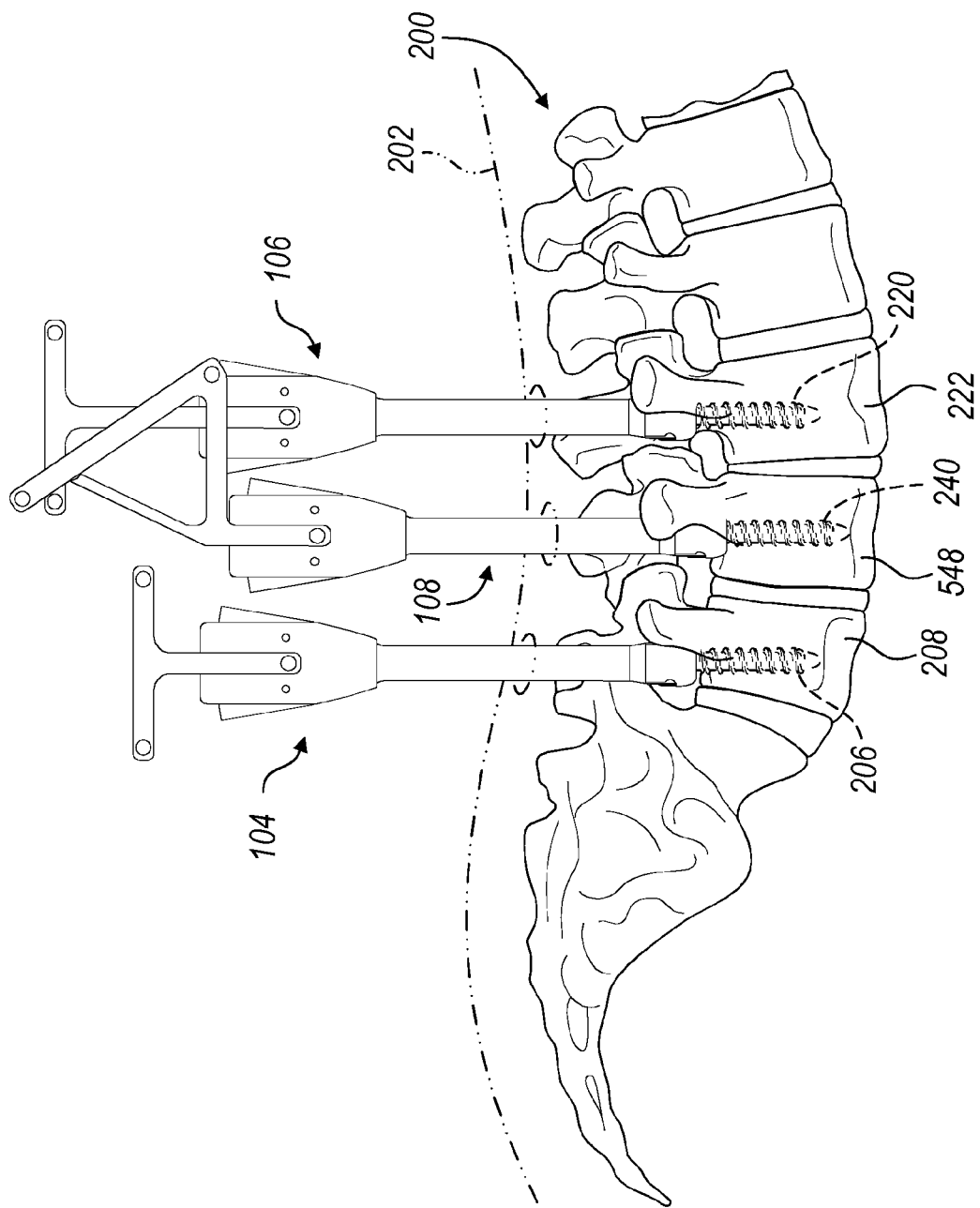
FIG. 10A is a partial detailed view of the spine including three portions of a construct including localization elements affixed thereto according to various embodiments.

With continuing reference to FIG. 9A, once the alignment has been selected, such as the alignment of alignment line 226 and the alignment of alignment line 230, as only an example, a navigated instrument may be used to achieve a selected location and trajectory of a third screw 240 (FIG. 10A) such as determining a location and trajectory of a third member in block 166. Any appropriate instrument may be used to select and navigate a trajectory of the third screw 240. For example, a navigated needle may be used to achieve the initial location and trajectory of the third screw in a third vertebrae 234 (FIG. 10A).

Figure 9B:
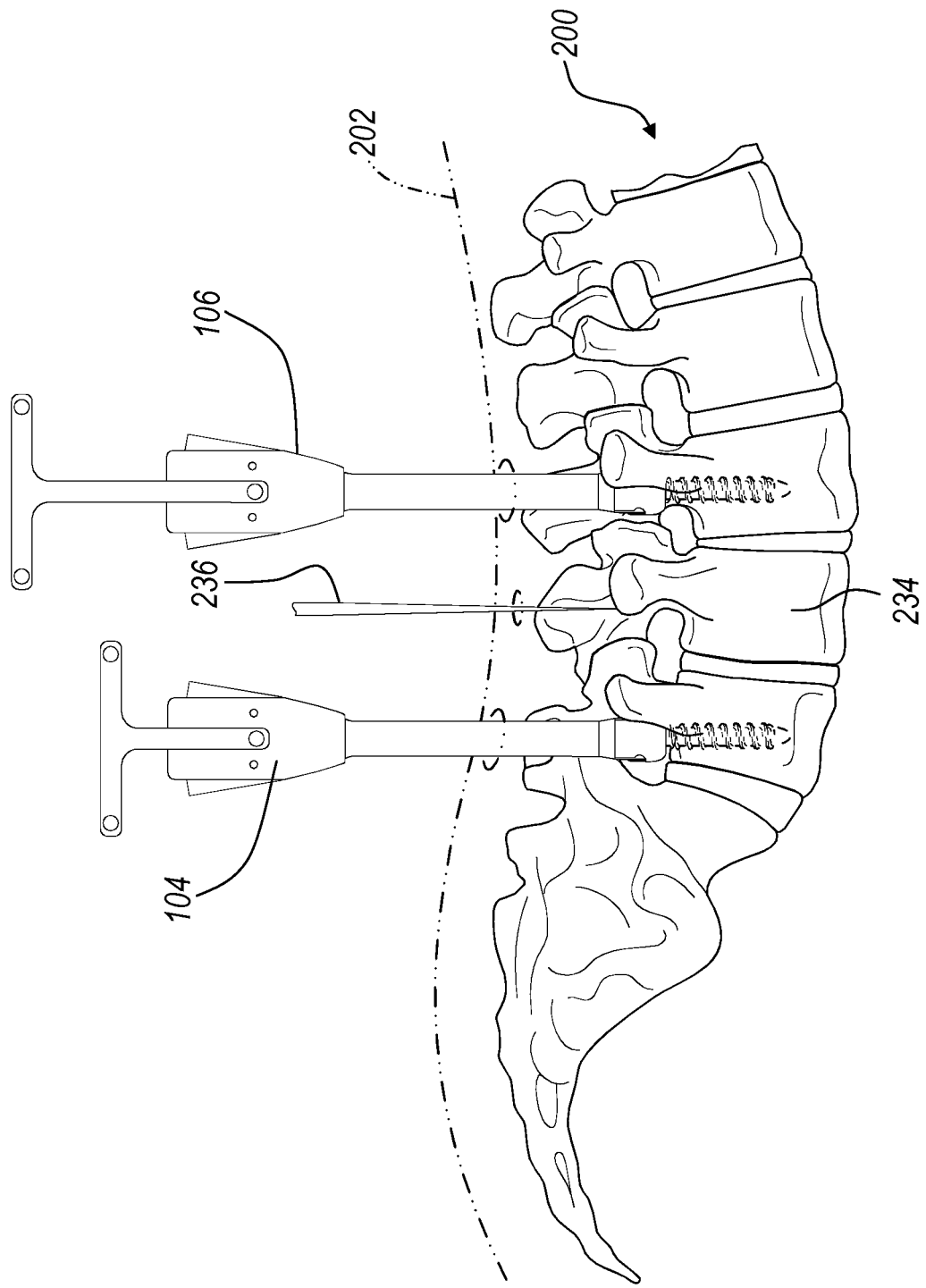
FIG. 9B is a partial detailed view of a portion of the spine including an element to assist in positioning a third portion of the construct.

With continuing reference to FIG. 9A and additional referenced to FIG. 9B a navigated needle 236 may be used to touch one or a plurality of points on the third vertebrae 234.

The navigated needle 236 may use any appropriate navigational location system and may include a locating or tracking element, such as those described above, such that the detector 22 may detect the location of the needle 236 and it may be displayed on the monitor 28. A virtual navigated needle 236' may be shown as a crosshair in the AP section 212 of the screen 210 and may be shown as a pointer in the lateral plane view section 216. In addition, a optimal location 238 may be shown on the screen 210 as a circle or other indication for locating a trajectory of the third screw. Therefore, the navigated needle 236 may be used to illustrate a virtual navigated needle location 236' on the screen 210 such that the navigated needle 236 may be moved until it substantially intersects the optimal location 238 illustrated on the screen 210. The navigated needle 236 may then be used to form a pilot hole or point in the third vertebrae 234 for initial locating and driving of the third screw.

The navigating computer 24 may form the optimal location 238 displayed on the monitor 28 as a location on the screen 210 such that the navigated needle 236 may be moved to substantially reach in the anatomical spine 200 the optimal or suggested location illustrated on the screen. The virtual navigated needle 236' allows the user to move the navigated needle 236 and see a location of the navigated needle 236 on the screen 210 as the virtual navigated needle 236' such that the navigated needle may be moved relative to the spine 200 without the user actually viewing the spine 200 or a tip of the needle 236. The navigation computer 24 may calculate the optimal location 238 for placement of the third screw due to the selection of the alignment planes 226 and 230.

Once the navigational needle 236 has reached the optimal location 238 determined by computer 24 or selected by the user the third screw 240 may be inserted into the third vertebrae 234. The third screw 240 may be inserted into the position pierced with the navigation needle 236. The piercing by the navigation needle 236 may provide an initial trajectory for placing the third screw 240 into the third vertebrae 234. Nevertheless, to insure the achievement of the selected radii, the third screw 240 may need to be inserted to a selected depth. Therefore, the third screw 240 may be navigated using the navigation computer 24 to display the screen 210 that includes the third screw 240 as a third virtual screw 240'.

With reference to FIG. 10A, the positioning of the third screw 240 may be guided and navigated using the navigation computer 24 and viewing the virtual third screw 240' on the screen 210. Alternatively, navigation needle 236 may be used to engage a top of the third screw 240 thus allowing the determination of the position on the third screw 240 for displaying the third virtual screw 240'. Alternatively, the third location element 108, including the tracking element 114 positioned on the extender 136, may engage the third screw 240. Using the substantially quick release mechanism the localization element 108 may be quickly engaged and disengaged from the third screw 240. Therefore, the third screw 240 may be positioned in a first location and the localization element 108 be positioned relative to the third screw 240 and a location of the third screw 240 be determined.

Figure 10B:
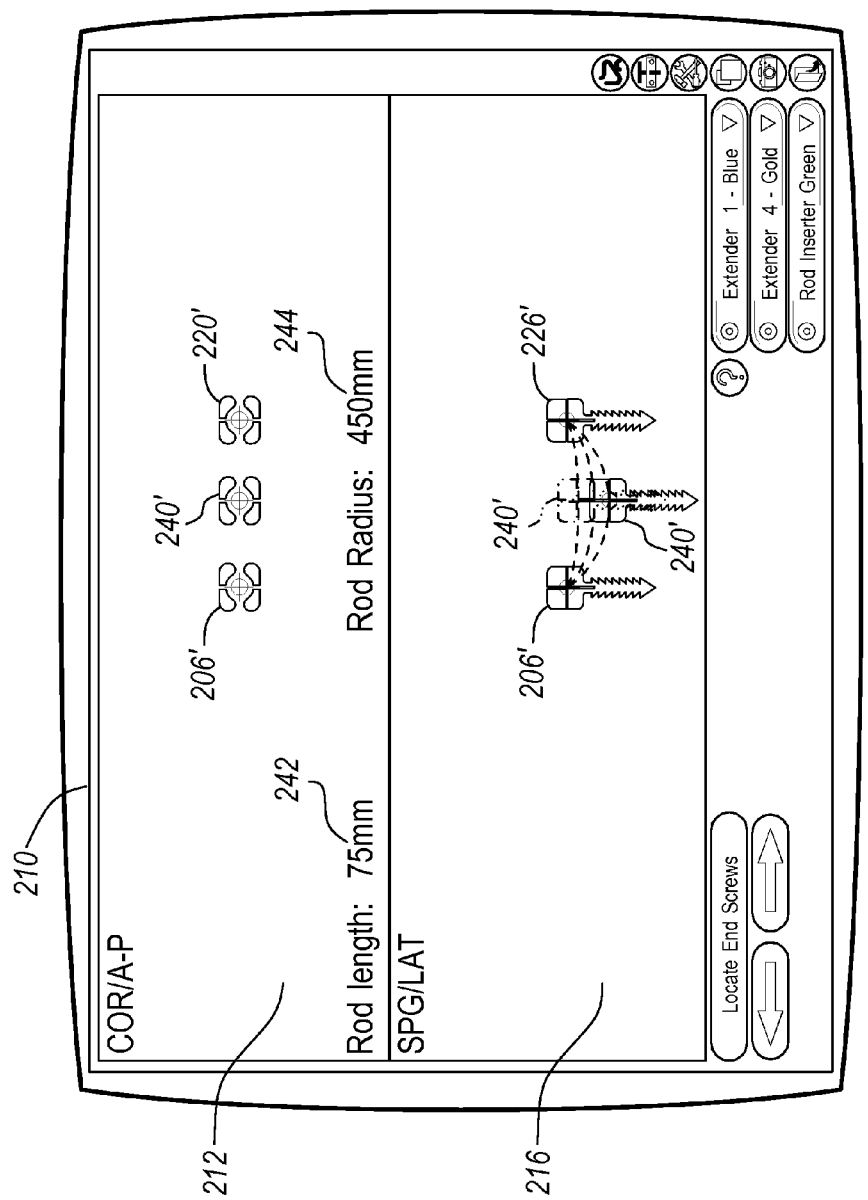
FIG. 10B is a screen produced by the surgical navigation system to assist in positioning a third member of the construct.

The first position of the third screw 240 may be illustrated as 240' in phantom as illustrated in FIG. 10B. The phantom location of the virtual screw 240' may indicate that the third screw 240 must be further driven into the third vertebrae 234 to achieve the selected location. Therefore, the location element 108 may be removed from the third screw 240 such that the third screw may be driven further into the third vertebrae 234. After the adjustment of the third screw 240 the localization element 108 may be reengaged to the third screw 240 and the location again determined of the third screw 240. This process may be repeated any appropriate number of times to guide the positioning of the third screw such as guiding the positioning of the third member in block 170. It will also be understood that any appropriate mechanism may be used to navigate the movement of the third screw 240. As discussed above, various mechanisms may either be included in the third screw 240 or attached to the third screw 240 rather than using the imaged based system. Nevertheless, the positioning of the third screw 240 can be substantially navigated using the navigation computer 24 such that the placement of the third screw 240 can be substantially precisely placed.

It will be understood that very precise placement of the third screw 240, or any of the screws 206 and 220, may not be necessary when a non-rigid fourth member or connector is used. For example, the third screw 240 may be navigated to a selected position, such as one to insure a selected purchase in the third vertebrae 234, and a deformable connector may then be used to interconnect each of the screws 206, 238, and 240. The flexible or deformable connector may be an injectable catheter, a cord, or other appropriate deformable connector. Therefore, it will be understood that the navigation of the positioning of the third screw 240, or any of the screws 206, 220 or any other number of screws, may be navigated such that the screws achieve a selected characteristic, such as a purchase in the selected vertebras, and a deformable or selected connector may be used to interconnect the various screws.

When a rigid connector is being used, however, the screen 210 and the navigation computer 24 may be used to determine a characteristic of a connector. For example, with reference to FIG. 10B, if a rigid rod is being used to interconnect the screws 206, 220, and 240, the display may indicate a rod length 242 and a rod radius 244. Therefore, the navigation computer 24 may assist in the selection of an appropriate rod and assist in placing the screws 206, 220, and 240 to achieve this selected rod characteristics. The determination of the appropriate rod and characteristics may be similar to that performed in block 172.

After the appropriate characteristic or selected characteristic is determined, the plan, including the selected rod to interconnect the screws 206, 220, and 240, may be determined such as determining the plan and selection of fourth member block 174. After the plan is determined, the user may either reject the plan such as in block 176 or accept the plan in block 178. If the plan illustrated on the screen 210 is rejected the third screw 240 may be navigated to a different position. Therefore, the steps described above may be repeated to position the third screw 240 in a different selected location and which may be illustrated on the monitor as the virtual third screw 240'. Again, the localization element 108 may be used to determine the location of the third screw 240 and illustrate the location of the third screw 240 on a screen 210.

If the plan for selection of the connector is accepted, as in block 178, the rod may be operably interconnected with a navigable instrument. With reference to FIG. 5, the connector 88 may include the exemplary rod 92 which includes the selected characteristics, such as a rod length of 75 mm and a rod radius of 196 mm. Nevertheless, it will be understood that different connectors may have different radia and lengths.

Nevertheless, the rod 92 is generally interconnected with the instrument 36 which includes the tracking element 230. The rod 92 is generally fixed at the proximal end 92b to a portion of the instrument 36 that is able to substantially selectively hold the rod 92 during the implantation. The selection of the rod may then be accepted or inputted into the computer 24 such that a computer 24 knows the length of the rod 92 extending from the instrument 36. The rod 92 and its distal endpoint 92a may then be calibrated and verified, such as in block 186. This may include the stored data regarding the rod 92 or through various tests to locate the distal end 92a of the rod 92 in the instrument 36. Therefore, because the rod 92 and the instrument 36 have been calibrated, the navigation computer 24 is able to determine the location of the distal end 92a of the rod 92 by the detection by the detector 22 of the tracking elements 230 affixed to the instrument 36. Nevertheless, it will be understood that any appropriate tracking element may extend or be incorporated with the instrument, such as various EM coils. In addition, the rod 92 may include various tracking elements such as coils that may be detected in an EM navigation system or other appropriate navigation systems. Nevertheless, regardless of the apparatus or method chosen, the location of the rod 92 is able to be determined by the navigation computer 24 and navigated and illustrated on the screen 210.

Figure 11A:
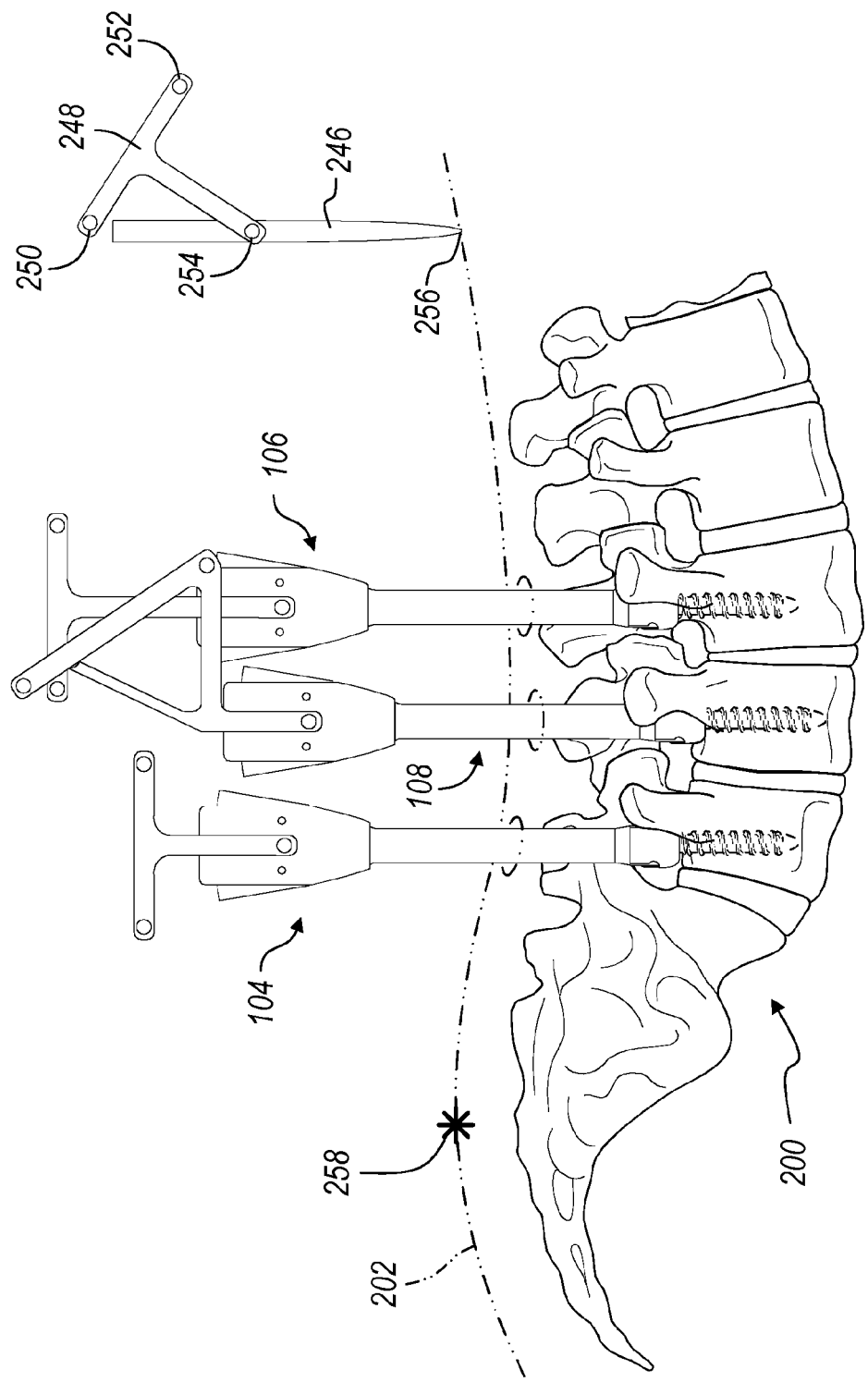
FIG. 11A is a partial detailed view of the spine including a probe to determine a contour of soft tissue surrounding the spine.
Figure 11B:
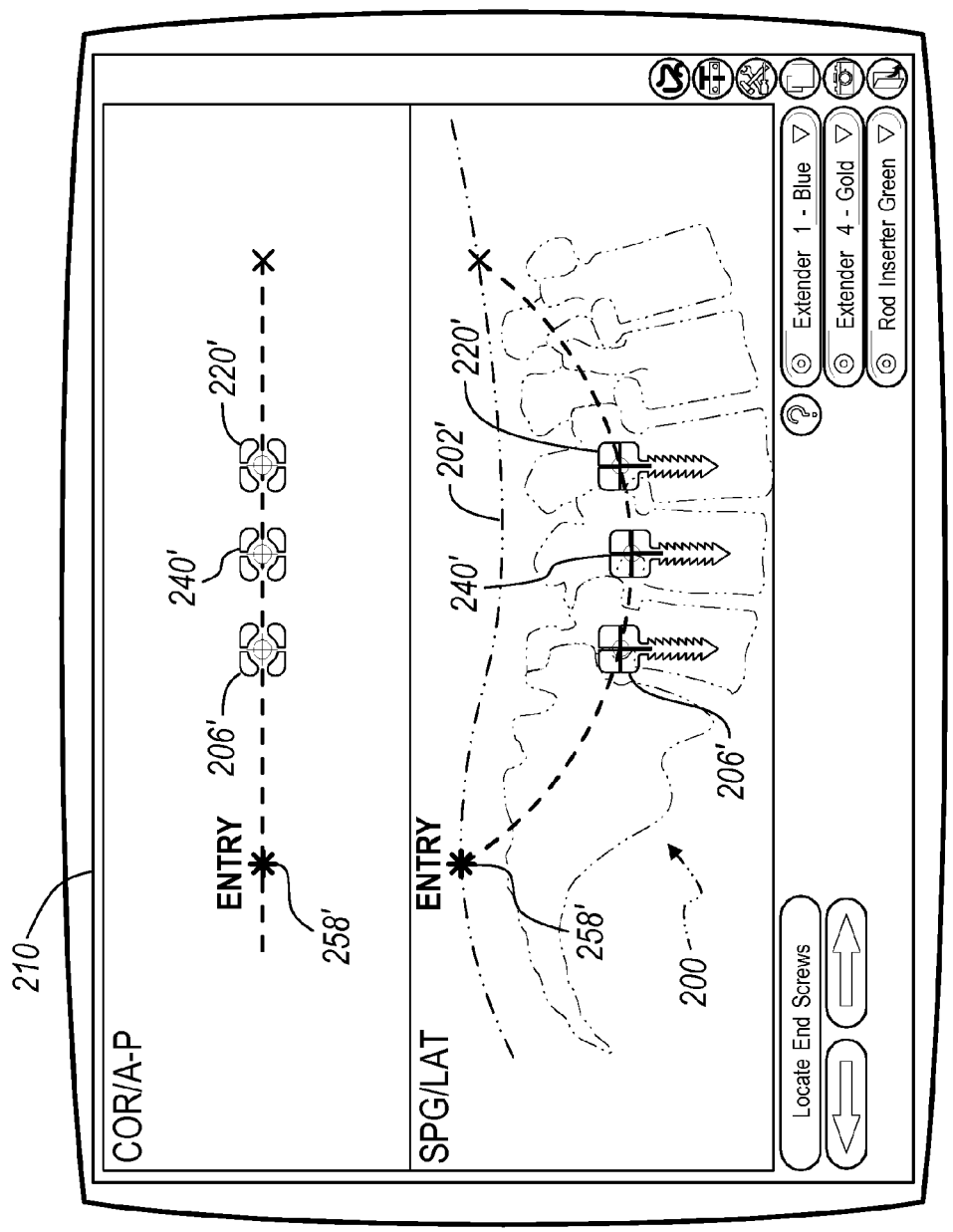
FIG. 11B is a screen produced by the surgical navigation system including an optional image of the anatomical portions.

With reference to FIGS. 11A and 11B the position of the dermis 202 may be determined relative to the spine 200. Although, as discussed above, determining the location of the soft tissue 202 relative to the spine 200 is not necessary. It may assist in determining an appropriate path of the rod 92 through the screws 206, 220, and 240. Therefore, a selected instrument such as the dermal topography instrument 246 may be used to trace or determine various points of the dermis 202. The dermis topography instrument 246 may include a tracking element 248 that includes navigation points 250, 252 and 254. As discussed above, the tracking element 248 may be detected using the detector 22 to determine a location of a distal tip 256 of the dermal topography instrument 246. The dermal topography element 246 may be traced over or touched to a plurality of points on the dermas 202 such that a virtual dermal layer 202' may be illustrated on the screen 210. Therefore, the dermal layer or location of the soft tissue may be illustrated on the screen 210 and location determined such as determine a location of selected soft tissue in block 180.

After the dermal tissue has been located and illustrated on the screen 210 an entry point 258 may be selected or determined with the navigation computer 24 and illustrated as a virtual entry point 258' on the screen 210. Therefore, the location of a entry 258 may be selected depending upon the topography of the dermis and other selected soft tissues. Nevertheless, it will be understood that the determination of an entry point such as in block 182, may be determined without providing an outline of the dermas 202. In addition, the entry point may be selected by a user regardless of the topography of the dermas and may be selected based upon other considerations. Nevertheless, the navigation computer 24 is able to illustrate the dermal layer 202 relative to the screws 206, 220, and 240 on the screen 210. In addition, as discussed above, a virtual spine may overlay the virtual screws 206', 220' and 240' on the screen 210. Therefore, a substantially complete anatomical view may be displayed on the screen 210 including both an outline of the dermas 202 as a virtual dermal outline 202' and a spine.

It will also be understood that if the fluoroscopic device 50 is included that an image may be taken at any appropriate time to confirm the location of the screws 206, 220, and 240 in the spine 200 as located on the screen 210. Therefore, an image may be taken intra-operatively, or at any other appropriate time, to confirm the location of the screws in the spine 200. This image may also be viewed on the screen 210 rather than a preoperative or a atlas image.

Figure 12A:
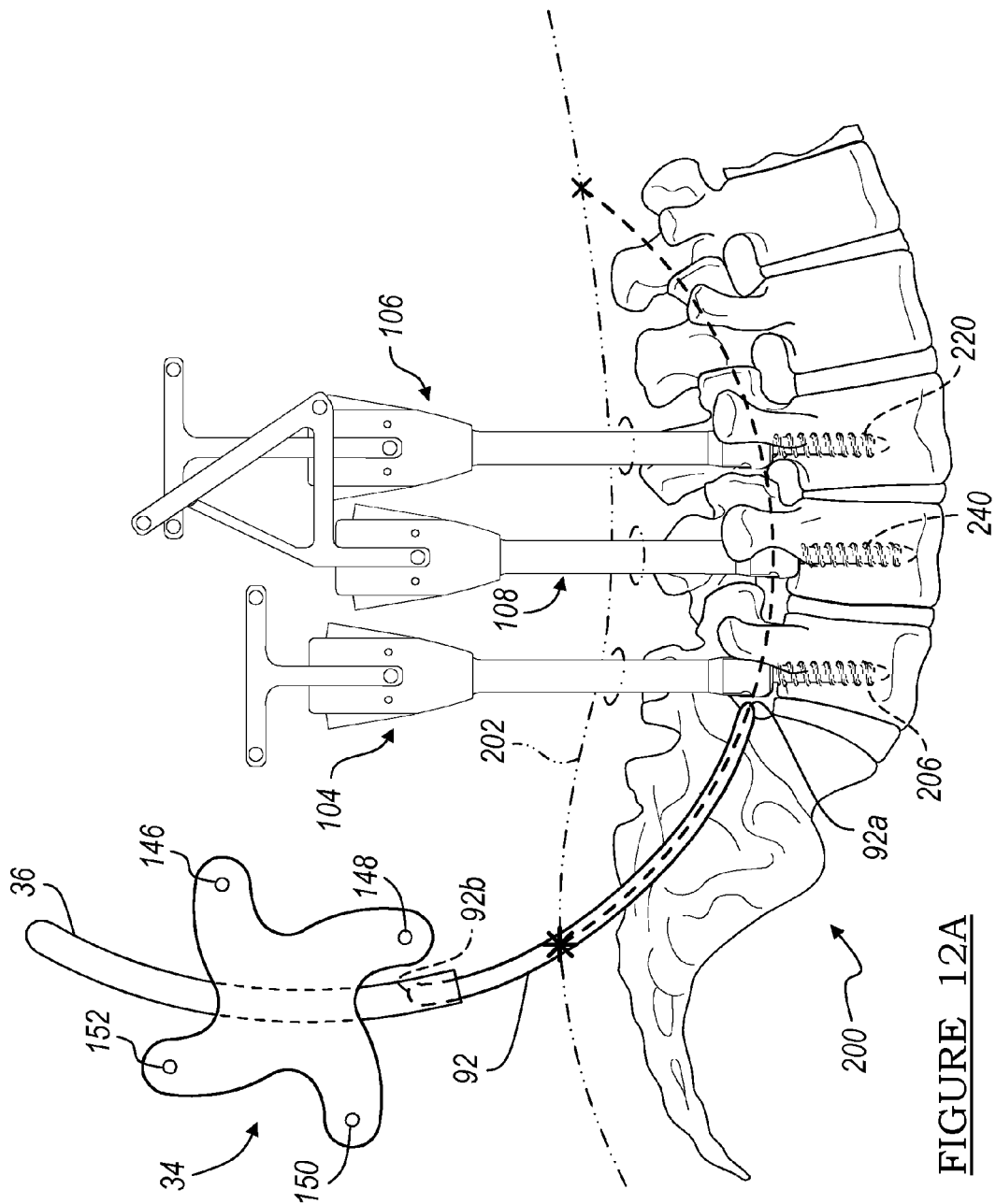
FIG. 12A is a partial detailed view of the spine including a connector that is navigable relative to other construct portions.
Figure 12B:
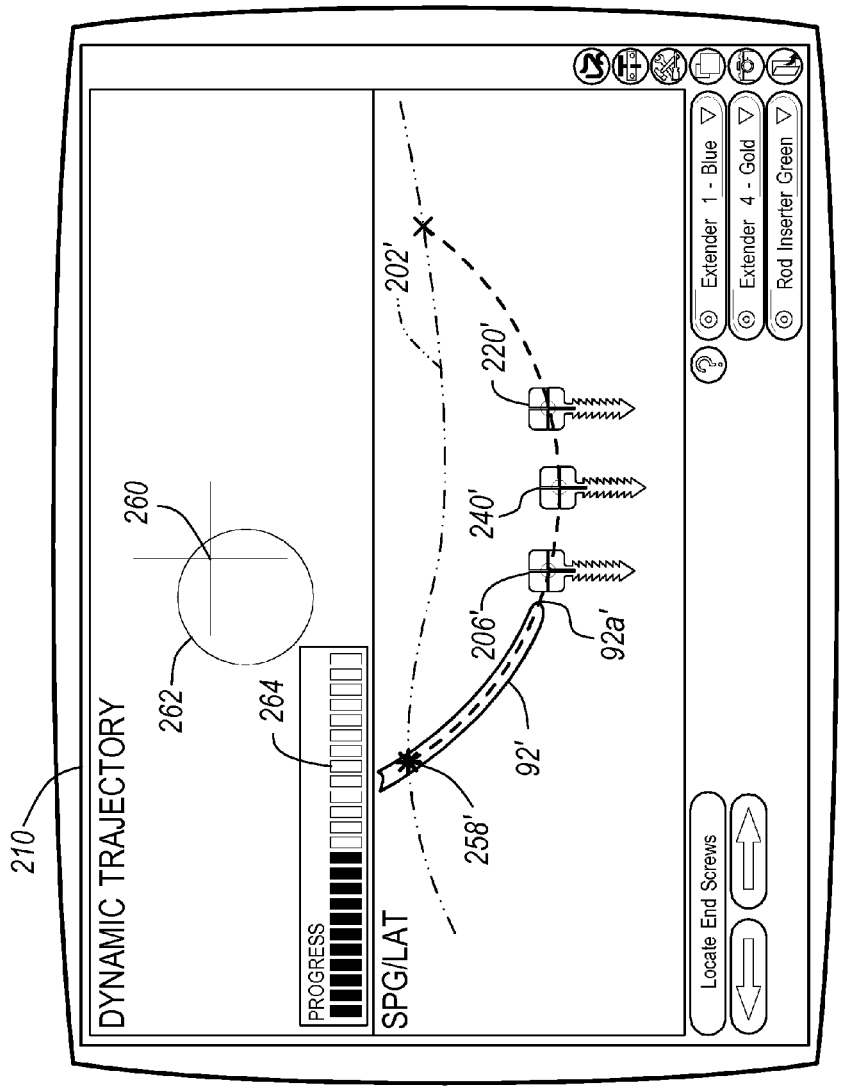
FIG. 12B is a virtual view of the connector interconnecting the various portions of the construct and assisting in the navigation thereof according to various embodiments.

With reference to FIGS. 12A and 12B after the rod 92 has been calibrated relative to the instrument 36, the implantation of the rod 92 may proceed. With particular reference to FIG. 12B the first section 212 of the screen 210 may change to a Dynamic Trajectory view of the distal end 92*a* of the rod 92 being illustrated as a crosshair 260 relative to a circle or other appropriate shape as a desired path 262. The progress of the rod 92 along the planned route may also be illustrated as a bar or other graphic 264. It will also be understood that the progress may be illustrated using a numerical indication, such as a percent.

The distal end 92*a* of the rod 92 is localized, prior to the beginning of the procedure, such as in block 188. After the distal end 92*a* of the rod 92 has been localized, the navigation computer 24 may be used to navigate and illustrate the movement of the rod on the screen 210. Therefore, the movement of the rod may be tracked such as the fourth member may be tracked and guided, such as in block 190. the position of the distal end 92*a* of the rod 92 is illustrated as the crosshair 260 such that the user is able to determine whether the distal end 92*a* of the rod 92 is positioned relative to the desired path as illustrated as a desired path 262.

In addition to the numerical graphical progress illustrated in the first part 212 of the screen 210, a virtual location of the rod 92 may be illustrated as the virtual rod 92' on the lateral plane view of the screen 210. In addition, the distal tip 92*a* may be illustrated as a virtual distal tip 92*a*'. Therefore, a virtual image of the progress of the rod 92 may be illustrated on the monitor 28 as determined by the navigation computer 24. The position of the rod 92 is known and may be determined due to the fact that the rod 92 is generally fixed to the instrument 36 which includes the tracking elements 230. The detector 22 may detect the tracking element 230 to determine the position of the instrument 36 and the navigation computer 24 is able to then determine the location of the rod 92 and the distal tip 92*a*. The position and movement to the distal tip 92*a* can be known and illustrated as the virtual distal tip 92*a* or the crosshair 260. In this way, the position of the distal tip 92*a* of the rod 92 can be illustrated for both determining and insuring that the distal tip 92*a* is moving along the selected path 262 and the virtual progress of the rod 92 through the spine 200. Therefore, the progress of the rod 92 may be indicated as the progress of the fourth member in block 192.

It will be understood, however, that the rod 92 may also include other tracking elements, such as coils that may be detected with an EM detector, rather than including the tracking element 230 on the instrument 36. In addition, the connector 92 or a similar connector, may not necessarily be a substantially rigid member. Rather the connector may be a substantially navigable or steerable catheter which may be steered relative to the screws 206, 220, and 240. Therefore, the dynamic trajectory section of the screen 210 may illustrate or show the distal end of the steerable catheter relative to the selected path 262. Nevertheless, the selected path, 262 may be generally discontinuous such that the steerable catheter may be steered to achieve the selected path 262. Therefore, the steerable catheter may be inserted relative to the screws 206, 220, and 240 in a selected manner using the navigation computer 24 and the monitor 28 such that a substantially complex interconnection can be formed without a generally open procedure to completely view the spine 200.

Figure 13A:
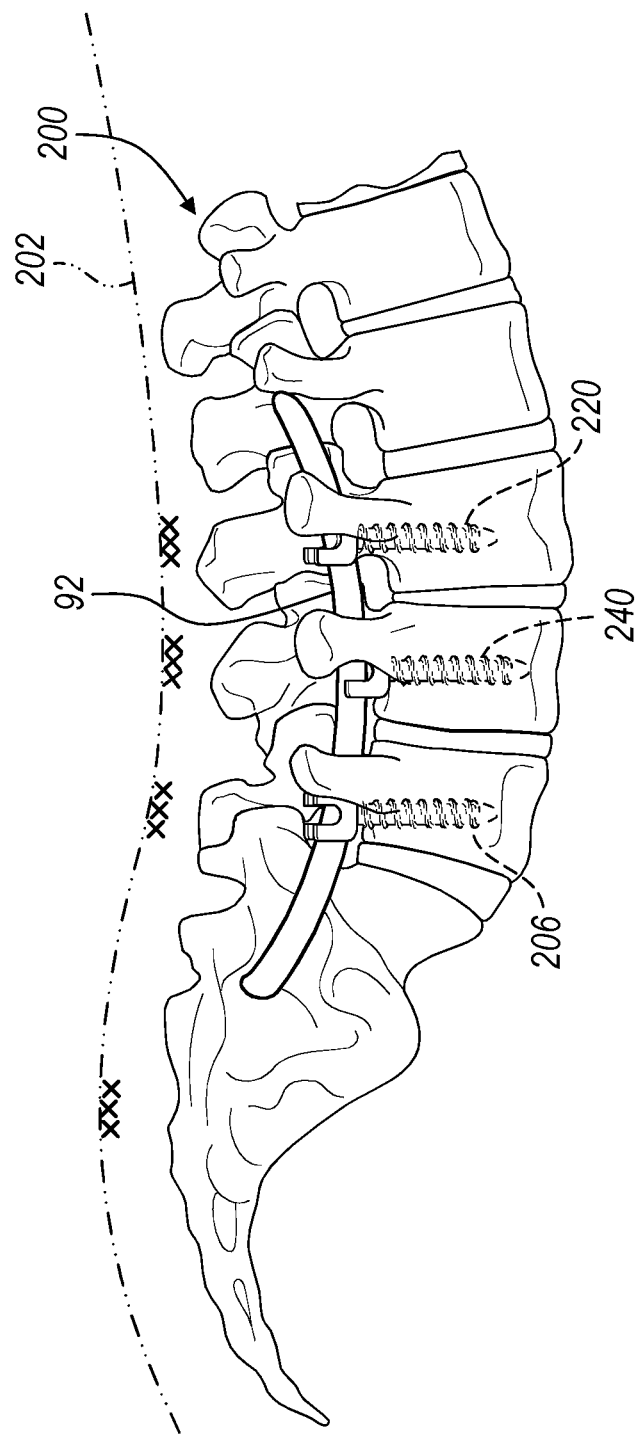
FIG. 13A is a partial detailed view of the spine including the construct assembled.
Figure 13B:
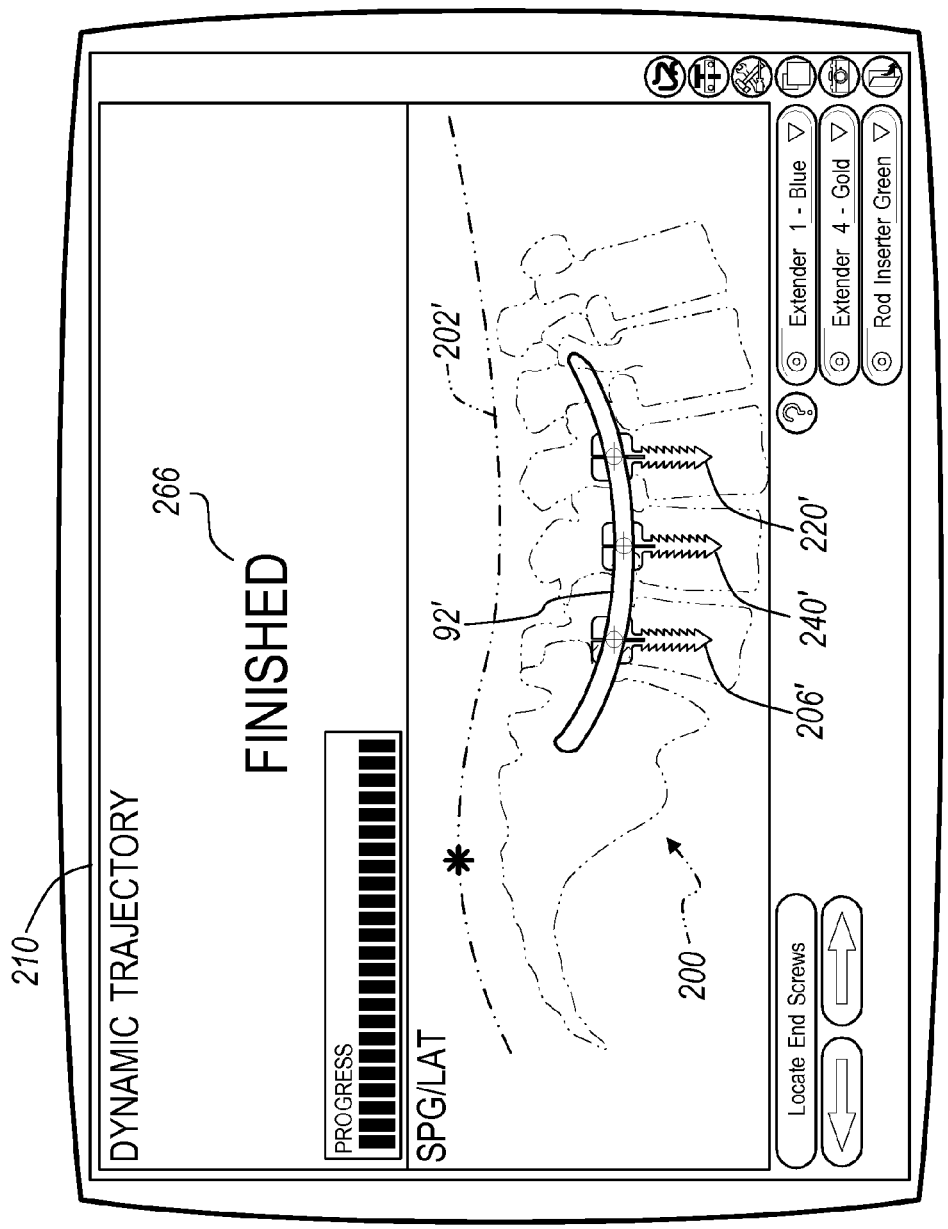
FIG. 13B is a screen produced by the surgical navigation system to indicate completion of the procedure and optional confirmation using the optional imaging system.

With reference to FIGS. 13A and 13B, the connector 92 may generally interconnect each of the three screws 206, 220, and 240. The navigation of the connector 92 may also be useful in determining the achievement of the distal end 92*a* of the connector 92 at the pre-selected end point relative to the one of the screws. As exemplary illustrated here the second screw 220 substantially defines an end point of the movement of the connector 92. Therefore, the navigation computer 24 is able to determine the achievement of the end point by the fourth member such as in block 194. The screen 210 may illustrate this achievement of the end point by illustrating the virtual rod 92' positioned at a selected position relative to the virtual screws on the screen 210. In addition, various indications such as word indications 266 including FINISHED may be illustrated on the screen 210 to notify the user that the predetermined plan has been achieved. In addition, the virtual rod 92' may change colors, an audible signal maybe created, or any other appropriate signal may be used to signal the user that the predetermined plan has been achieved. Generally, the procedure is then ended such as in block 196. Nevertheless, various other actions may be taken such as removing the instrument 36 from the rod 92, suturing the incisions formed for the insertion of the screws, and removing the localization elements 104, 106, and 108, or any other appropriate measures that are selected to be taken to complete the implant procedure. In addition, after the various localizers and other elements are removed, the screws are generally tightened onto the connector 92. This may occur in any appropriate manner, such as locking the multi-access screws in a selected position, tightening the screw relative to the bone to hold the connector 92 relative to the bone, or any other appropriate manner. Generally, the navigation allows the connector to be positioned relative to the screws and afterwards, the screws are locked relative to the connector.

In addition, the optional imaging system 50 may be used to acquire an image of the patient 40 for display on the monitor 28. The optional image acquired of the patient 40 may also be used to confirm proper placement of the construct 88 in the patient 40. Also, as illustrated in FIG. 13B, the acquired image of the patient 40 may be superimposed over the icons representing the screws 206', 220' and 240' and the rod 92', to confirm proper or selected placement of the construct. Again, as discussed above, an image of the patient 40 is not required to perform the procedure thus the optional imaging system 50 is not necessary to acquire an imaging of the patient 40.

Therefore, the construct 88 may be implanted in the patient 40 through a substantially minimally invasive procedure. The incisions though the dermis 202 may be kept small thus reducing trauma and minimizing direct visualization of the anatomy. Nevertheless, the imageless navigation system 20 may be used to track, guide and assist in the implantation percutaneously.

According to the above, a multi-level or geometrically constrained construct, such as the spinal implant 80, may be implanted relative to a spine through a substantially less invasive or percutaneous procedure. The implantation of the construct 80 relative to the spine 200 may include a plurality of elements, such as the three or more screws 206, 220, and 240 or any appropriate number of screws and the connector 88 to interconnect each of the screws. Although the above discussion included three screws only one or more than three may be used. In addition, the navigation computer 24 may be used when the connector 88 is of a selected and/or constrained geometry.

The navigation computer 24 may be used to navigate the connector relative to the plurality of screws such that a selected position, which may be a substantially complex position, of the connector can be achieved. In addition, the selected position of a connector may be achieved without substantially mechanical means or apparatus required to move the connector relative to the screws. Rather, the navigation computer 24 is able to navigate the connector, such as the rod 92, relative to the other elements of the construct.

Although the above discussion has exemplary illustrated the method to implant a construct relative to a spine it will be understood that any other appropriate construct may be implanted. For example, the navigation system may be used to navigate an acetabular implant substantially percutaneously. The positions of the acetabular implant may be determined using localization or tracking elements and the placements of other elements relative to selected portions of the anatomy or other portions implanted may be navigated with the navigation computer. Therefore, the navigation computer 24 may be used to navigate the implantation of any appropriate implant through a generally percutaneous and/or minimally invasive procedure.

It will be understood that the above is merely exemplary of applications of the present disclosure and appended claims. For example, although the above description is related to implanting a connector relative to a plurality of screws, it will be understood that the information collected into the navigation computer 24 may also be used to customize a connector. Therefore, a connector may be bent either manually or automatically to interconnect the plurality of screws. In addition, a kit may include a plurality of connectors, such as the kit illustrated in FIG. 3, to allow for the selection of a connector that substantially interconnects the screws 82 in a selected manner. Therefore, the method 146 may be used to implant a connector relative to a plurality of screws in any appropriate manner. Also, the navigation computer 24 and the method 146 generally allows for the connection of a plurality of points, such as three or more. Therefore, a complex geometry, such as a constrained geometry, can be easily achieved by use of the presently described invention. Therefore, a mechanical alignment device is not necessary, though it may be used.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A system for use in navigating an implantation of a selected construct, comprising:
 a first member having an open passage to receive a second member, wherein the second member is configured to be received and connected within the open passage of the first member after implantation;
 a first localization element selectively connectable and fixed to said first member by at least partially encompassing a portion of the first member and engaging at least the encompassed portion of the first member with an internal mechanism during a navigation of the second member relative to the first member;
 a second localization element simultaneously selectively connected to said second member when said first localization element is selectively connected and fixed to said first member;
 a detector to detect said first localization element and said second localization element while both said first localization element is connected to said first member and said second localization element is selectively connected to said second member;
 a display device; and
 a processor configured to navigate said second member relative to said first member;
 wherein said processor is operable to receive position information for both of said first member and said second member from said detector both while said first localization element is connected to said first member and while said second localization element is selectively connected to said second member and further operable to determine a relative position of said first member to said second member;
 wherein said processor is configured to distinguish the location of said first localization element that is different from said second localization element;
 wherein said relative position is operable to allow a navigated movement of said second member to said first member to connect said first member and said second member substantially only by detecting positions of said first localization element and said second localization element and the display device illustrates only icons representing the first member and the second member.

2. The system of claim 1, wherein said first member is configured to be positioned beneath a tissue and said second member is configured to move beneath the tissue to be connected with said first member.

3. The system of claim 2, wherein said first localization element is configured to remain fixed to said first member during the navigation.

4. The system of claim 3, wherein said second member is configured to be moved in a volume between said first localization element and said first member.

5. The system of claim 3, further comprising:
 an extending member that is configured to extend through the tissue and include the internal mechanism, wherein said first localization element is coupled to said extending member to be exposed to said detector when associated with said first member.

6. The system of claim 5,
 wherein the first member is a screw and the extending member is keyed to engage the screw in substantially a single position to determine six degree of freedom position information of said screw;
 wherein said six degree of freedom information is displayed with said display device.

7. The system of claim 6, further comprising:
 a third member that is a screw configured to be interconnected to the first member and the second member to form the construct; and
 a third localization element configured to be connected to the third member during navigation of the second member relative to the first member and the third member where the third localization element extends through the tissue when the third member is covered by the tissue;
 wherein said second member is configured to be fixedly connected to said first member and said third member in a selected connected configuration;
 wherein said connected configuration is based on an alignment in at least one plane defined relative to an anatomy;
 wherein said display device is configured to display an alignment icon based on the alignment in at least one plane relative to a display of relative positions of at least the first member and the third member.

8. A method for navigating an implantation of a construct, comprising:
 detecting with a detector a first localization element connected to a first member of the construct, wherein said first member is implanted into a first anatomical structure of an anatomy;
 detecting with said detector a second localization element selectively connected to a second member of the construct, wherein the second member is moveable relative to the first member;
 determining a first position of said first member based on position information received by a processor from said detector regarding said first localization element and simultaneously determining a second position of said second member based on position information received by the processor from said detector regarding said second localization element;
determining an alignment of said second member relative to said first member; and
displaying the first position of said first member relative to the second position of said second member at least while the second member is positioned within a portion of the first member that is implanted into the first anatomical structure of the anatomy to achieve said determined alignment once said first member and said second member are fixedly connected;
wherein displaying the first position of said first member relative to the second position of said second member includes displaying on a display device only icons for viewing a representation of navigated portions including at least one of a selected path icon, a distal tip icon, a first icon illustrating a location of the first member, and a second icon illustrating a location of the second member.

9. The method of claim 8, further comprising:
fixedly connecting said second member to said first member.

10. The method of claim 9, further comprising:
detecting with said detector a third localization element selectively connected to a third member of the construct, wherein said third member is implanted into a second anatomical structure of the anatomy.

11. The method of claim 10, wherein determining said alignment of said second member relative to said first member includes:
detecting simultaneously all of said first localization element, said second localization element, and said third localization element; and
determining an alignment of said first member and said third member to be maintained by an interconnection of said first member and said third member with said second member.

12. The method of claim 11, wherein said alignment is one of a radius or a plane.

13. The method of claim 12, further comprising:
displaying said alignment with said display device;
wherein said processor is operable to determine said alignment.

14. The method of claim 11,
wherein the distal tip icon illustrates a present location of a distal tip of the second member relative to the selected path icon.

15. The method of claim 14, further comprising:
navigating said second member relative to said first member using a display device including moving the second member relative to the first localization element that is selectively connected with the first member.

16. A system for use in navigating an implantation of a selected construct, comprising:
a first localization element has a depressible member that operates an internal mechanism to engage and disengage a head of a first member, wherein said first member includes a slot through which a second member is configured to be placed, said depressible member and said internal mechanism allow percutaneous engagement and percutaneous disengagement from said first member while a second member is navigated and moved to said first member and fixedly connected to said first member;
a second localization element fixed to said second member while said second member is moved to connect to said first member;
a detector to detect said first localization element and said second localization element;
a processor configured to receive position information for said first member from said detector based on detecting said first localization element and position information for the second member and is further configured to determine a relative position of said second member to said first member; and
a display device configured to display said relative position of said first member relative to said second member by displaying a first icon representing said first member and a second icon representing at least a portion of said second member without registering to patient images;
wherein said first icon and said second icon alone are operable to display location of said first member and said second member;
wherein said first localization element is configured to be removed percutaneously from said first member once said second member is connected to said first member.

17. The system of claim 16, further comprising:
said first member of the construct, wherein said first member of the construct is configured to be implanted into a first anatomical structure of an anatomy;
said second member of the construct, wherein said second member is configured to be fixedly connected with said first member after implantation;
said second localization element selectively associated with said second member;
wherein said processor is operable to receive further position information for said second member from said detector based on detecting said second localization element;
wherein said processor is further operable to determine a relative position of said second member relative to said first member with said position information for said first member and said second member.

18. The system of claim 17, wherein said first localization element has a first configuration and said second localization element has a second configuration;
wherein said first configuration and said second configuration are distinct from one another such that said processor is operable to identify said first member and said second member based on said selectively associated said first localization element and said selectively associated said second localization element.

19. The system of claim 18, wherein said first member is a screw and said first localization element is keyed to engage said screw in substantially a single position to determine six degree of freedom position information of said screw;
wherein said six degree of freedom information is displayed with said display device.

20. The system of claim 19, further comprising:
a third member of the construct configured to be implanted into a second anatomical structure of the anatomy; and
a third localization element selectively associated with said third member;
wherein said detector detects said third localization element;
wherein said processor is further operable to receive position information for said third member from said detector based on detecting said third localization element and further operable to determine relative positions of said first member, said second member, and said third member;
wherein said display device is configured to display said relative positions said first member, said second member, and said third member;

wherein said second member is configured to be fixedly connected to said first member and said third member in a selected connected configuration;

wherein said connected configuration is based on an alignment in at least one plane defined relative to the anatomy;

wherein said display device is configured to display an alignment icon based on said alignment relative to a display of at least said first member and said second member.

21. The system of claim 16, wherein said first localization element includes a cannula, wherein said cannula of said first localization element is configured to be aligned with a cannula of said first member;

wherein a guide wire is operable to be positioned within the cannula of said localization element and the cannula of said first member.

22. The system of claim 16, wherein the first localization element is keyed relative to said first member such that said first localization element is configured to allow determination of six degree of freedom position information of said first member.

* * * * *